(12) United States Patent
Perera et al.

(10) Patent No.: US 8,663,622 B2
(45) Date of Patent: Mar. 4, 2014

(54) RECOMBINANT VACCINE VIRUSES EXPRESSING IL-15 AND METHODS USING THE SAME

(75) Inventors: Liyanage P. Perera, Kensington, MD (US); Thomas A. Waldmann, Silver Spring, MD (US); Sang-Kon Oh, Baltimore, MD (US); Jay A. Berzofsky, Bethesda, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 338 days.

(21) Appl. No.: 10/538,974

(22) PCT Filed: Dec. 15, 2003

(86) PCT No.: PCT/US03/39967
§ 371 (c)(1),
(2), (4) Date: Nov. 29, 2005

(87) PCT Pub. No.: WO2004/058278
PCT Pub. Date: Jul. 15, 2004

(65) Prior Publication Data
US 2006/0147419 A1    Jul. 6, 2006

Related U.S. Application Data

(60) Provisional application No. 60/433,703, filed on Dec. 16, 2002.

(51) Int. Cl.
*A01N 63/00* (2006.01)
(52) U.S. Cl.
USPC ............... 424/93.1; 424/93.2; 424/93.21
(58) Field of Classification Search
USPC ............. 424/93.1, 93.2, 93.21; 514/44
See application file for complete search history.

(56) References Cited

U.S. PATENT DOCUMENTS

| 5,833,975 | A | * | 11/1998 | Paoletti et al. | 424/93.2 |
| 5,843,456 | A | * | 12/1998 | Paoletti et al. | 424/199.1 |
| 6,013,268 | A | * | 1/2000 | Reed et al. | |
| 6,190,901 | B1 | * | 2/2001 | Sundick et al. | |
| 6,656,471 | B1 | * | 12/2003 | Sastry et al. | 424/188.1 |
| 6,933,377 | B2 | * | 8/2005 | Chen | 536/23.72 |
| 2004/0105871 | A1 | * | 6/2004 | Robinson et al. | 424/199.1 |

FOREIGN PATENT DOCUMENTS

| WO | WO-96/11279 | 4/1996 |
| WO | WO 98/17799 | 4/1998 |
| WO | WO-99/27958 | 6/1999 |
| WO | WO-99/41402 | 8/1999 |
| WO | WO-99/51622 | 10/1999 |
| WO | WO-00/41508 | 7/2000 |
| WO | WO 01/55177 | * 8/2001 |

OTHER PUBLICATIONS

Perera et al, PNAS, 98(9): 51-46-5151, 2001.*
McMichael et al, Vaccine, 20: 1918-1921, 2002.*
Perera et al, PNAS, 98(9): 5146-5151, 2001.*
Giri et al, Clinical Microbiology Reviews, 17(2): 370-389, 2004.*
Xin et al, (Vaccine, 17: 858-866, 1999.*
Kim et al, (Virology, 285: 204-217, 2001.*
Robinson et al, (Nature Medicine, 5(5): 526-534, 1999.*
Waldmann et al, (Immunity, 14: 105-110, 2001.*
Carroll et al (Vaccine, 15(4): pp. 387-394, 1997).*
An et al (J Virol, 71(3): 2292-302, 1997).*
Waldman et al (Annu. Rev. Immunol, 17:19-49, 1999).*
Ward et al, PNAS, 92: 6773-677, 1995.*
Mackett et al, (J Gen Virol, 67: 2067-2082, 1986.*
Ward et al, PNAS, 92: 6773-677, 1995).*
Ravn et al (J Acquir Immune Defic Syndr Hum Huma Retrovirol, (Abstract), 1996).*
Becker et al (J. Exp. Med, vol. 195, No. 12, Jun. 17, 2002).*
Ahlers et al (AIDS Res Hum Retroviruses. 12(4): 259-262, 1996).*
Perera et al., Proceedings of the National Academy of Sciences, USA, 98(9):5146-5151 (2001).
Oh et al., Proceedings of the National Academy of Sciences, 100(6):3392-3397 (2003).
Moore et al., J. of Virology, 76(1):243-250.
Agostini et al., Blood, 90(3):1115-1123 (1997).
Kanai et al., J. Immunol., 157(8):3681-3687 (1996).
Kalams et al., "Safety and immunogenicity of an HIV-1 gag DNA vaccine with or without IL-12 and/or IL-15 plasmid cytokine adjuvant in healthy, HIV-1 uninfected adults", *PLoS ONE* 7(e29231):1-10 (2012).
Poon et al., "Vaccinia virus-based multivalent H5N1 avian influenza vaccines adjuvanted with IL-15 confer sterile cross-clade protection in mice", *J. Immunol.* 182:3063-3071 (2009).
Kolibab et al., "Highly persistent and effective prime/boost regimens against tuberculosis that use a multivalent modified vaccine virus Ankara-based tuberculosis vaccine with interleukin-15 as a molecular adjuvant", *Clin. Vaccine Immunol.* 17:793-801 (2010).
Merkel et al., "Development of a highly efficacious vaccinia-based dual vaccine against smallpox and anthrax, two important bioterror entities", *Proc. Natl. Acad. Sci. USA* 107:18091-18096 (2010).

* cited by examiner

*Primary Examiner* — Marcia S Noble
*Assistant Examiner* — Magdalene Sgagias
(74) *Attorney, Agent, or Firm* — Edwards Wildman Palmer LLP; Peter F. Corless

(57) ABSTRACT

The invention is directed to compositions capable of augmenting the immunogenicity of a vaccine. The composition, or adjuvant, is administered to a mammal in need thereof in sequential or concurrent combination with a vaccine antigen. In one preferred aspect, the adjuvant is provided in the form of a recombinant poxvirus vector, such as a vaccinia virus vector, which comprises a nucleic acid sequence encoding IL-15.

16 Claims, 12 Drawing Sheets

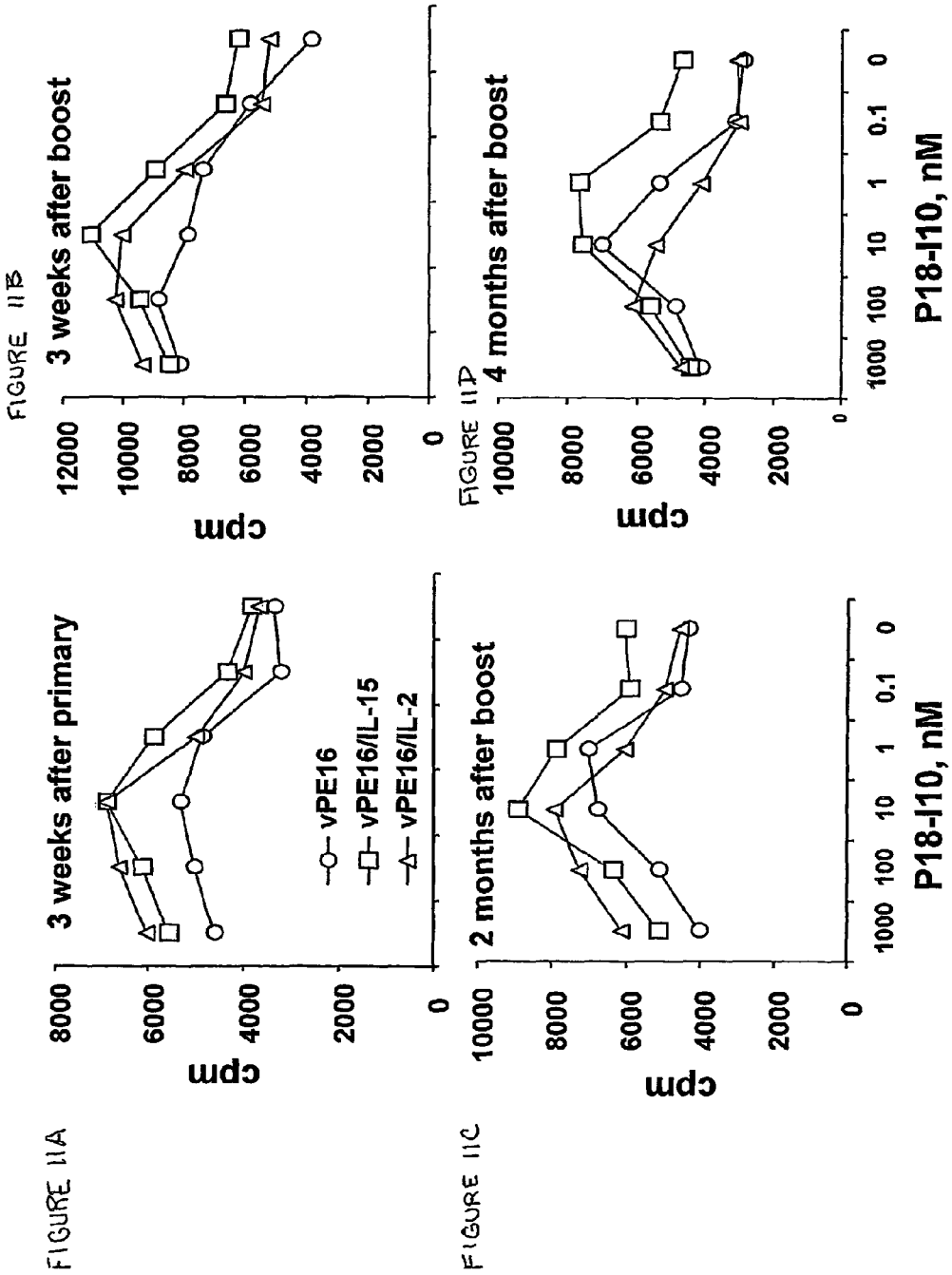

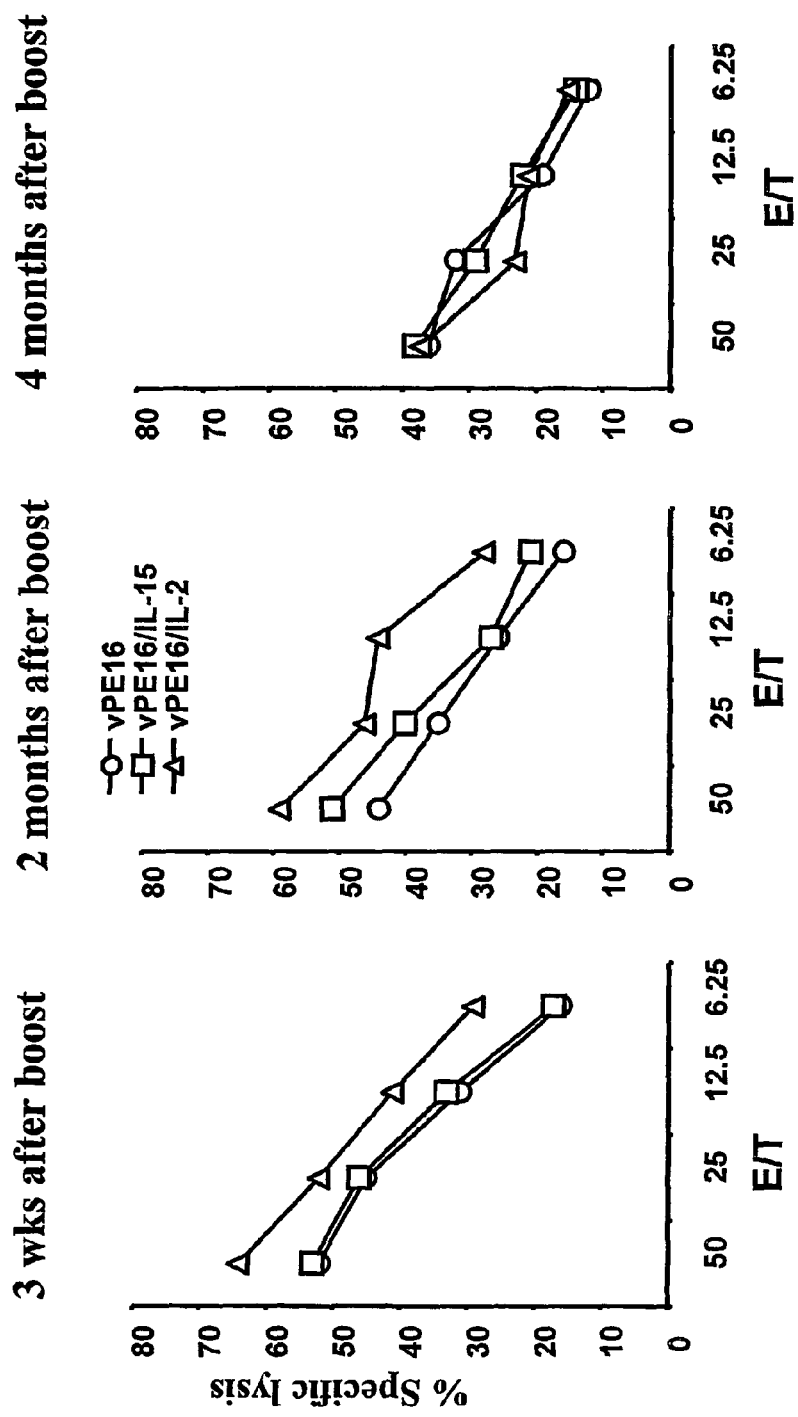

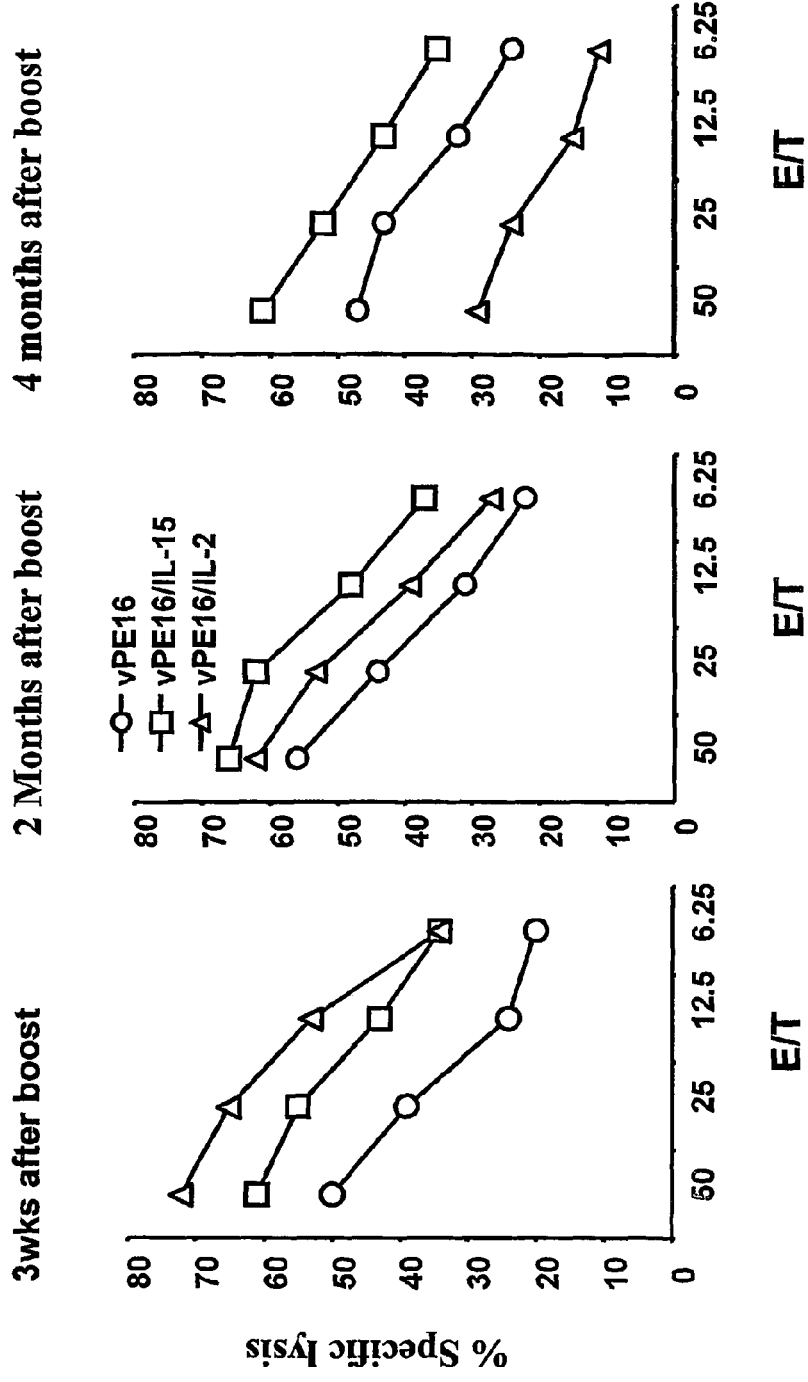

High avidity CD8+ CTLs induced with IL-15 persist longer period in vivo: 14 months after boost

RECOMBINANT VACCINE VIRUSES EXPRESSING IL-15 AND METHODS USING THE SAME

RELATED APPLICATION

This application claims priority to U.S. Provisional Application Ser. No. 60/433,703, filed Dec. 16, 2002, the entirety of which is incorporated by reference herein.

FIELD OF THE INVENTION

The invention relates to recombinant vaccine vectors capable of expressing interleukin 15 (ILpreferably is replication defective or incompetent or attenuated. Suitable vectors include, but are not limited to those based on (i.e., comprising portions of viral genomes of): poxviruses, adenoviruses, herpes viruses, alphaviruses, retroviruses, Epstein Barr viruses, lentiviruses, and picomaviruses. In one preferred aspect, the vector is a recombinant poxvirus vector. The recombinant nonvirulent poxvirus is preferably a vaccinia virus but may also be a fowlpox virus, such as a canarypox virus.

Preferably, the vector comprises one or more capsid polypeptides. In one aspect the one or more polypeptides are linked to a targeting molecule to facilitate selective infection of a cell (e.g., an antigen presenting cell, such as a dendritic cell, or a tumor cell).

Also preferably, the IL-15 encoding sequence comprises an expression control sequence operably linked thereto.

In one aspect, at least one antigen is a cancer specific antigen, such as an antigen from a Her-2/neu polypeptide.

In another aspect, at least one antigen is a bacterial antigen, for example, such as an antigen from *Borrelia burgdorferi*, *Bartonella henselea*, *Yersiulia pestis*, and *Bacillus anthracis*.

In a further aspect, at least one antigen is a viral peptide or polypeptide, for example a peptide/polypeptide expressed by a rabies viral genome, canine distemper virus genome, Newcastle disease virus genome, Ebola virus genome, West Nile virus genome, Epstein Barr virus genome or a smallpox genome.

In a particularly preferred aspect, at least one antigen comprises a viral peptide or polypeptide, such as a peptide or polypeptide expressed by an HIV or SIV virus genome.

The antigen encoding expression unit in some embodiments is a multivalent expression unit comprising a plurality of antigen encoding sequences. In one aspect, at least two antigens are from two different HIV polypeptides. In another aspect, at least two antigens are from two different strains of HIV. In still another aspect, at least two antigens are from two different isolates of HIV, or are from two different clades of HIV.

In still a further aspect, at least two antigens are from different subsequences of an HIV polypeptide. However, in another aspect, at least two antigens are derived from the same subsequence of an HIV polypeptide, but each subsequence differs by at least one amino acid. In one aspect, the subsequence is from a high mutable region in the HIV polypeptide.

In another aspect, the expression unit comprises a plurality of antigen encoding sequences, at least one antigen comprising a CTL-recognized epitope, at least one antigen comprising a T helper cell-recognized epitope, at least one antigen comprising a B cell-recognized epitope. In one aspect, the epitopes are from the same HIV polypeptide.

In one aspect, at least one antigen is from an HIV polypeptide while at least one other antigen is from an infectious organism associated with an opportunistic infection in HIV positive patients, e.g., such as *Pneumocystis cariini*.

The invention further provides a recombinant vaccine virus vector comprising a nucleic acid encoding IL-15 and a nucleic acid encoding at least one antigen, wherein the nucleic acid encoding at least one antigen is expressed by a second recombinant vaccine virus vector.

The invention also provides a method for generating an immune response in an animal comprising administering any of the recombinant vaccine virus vectors or compositions described above to an animal in an amount effective to stimulate the immune response. Preferably, the immune response comprises one or more of the production of memory $CD8^+$ T cells specific for the at least one antigen, the production of memory $CD4^+$ T cells specific for the at least one antigen, and the production of antibodies specific for the at least one antigen. Also, preferably, at least some of the antibodies are neutralizing antibodies.

In one aspect, the animal is a human being.

In another aspect, the animal is a domestic animal such as a dog or cat. The animal may also be a feral or wild animal such as foxes and raccoons. The animal may also be a non-human primate.

The method may be used to provide a prophylactic or therapeutic vaccine to a patient at risk for being infected with or already infected with a viral agent, such as smallpox or rabies. In one aspect, the method is used to provide a prophylactic vaccine to an individual at high risk of HIV infection and the vaccine may be administered to an individual who is not HIV positive at the time of first administration. However, the vaccine may also be administered to an individual who is HIV positive at the time of first administration.

Because the compositions according to the invention are able to potentiate a long-term immune response, re-administration of the composition may occur at longer intervals than vaccines of the prior art. In one aspect, the interval between a primary administration and re-administration of the recombinant vaccine vector is at least about 6 months, at least about 8 months, at least about 10 months, at least about 12 months, at least about 14 months, at least about 16 months, at least about 18 months, and at least about 24 months.

BRIEF DESCRIPTION OF THE FIGURES

The objects and features of the invention can be better understood with reference to the following detailed description and accompanying drawings.

FIGS. 11A-D are graphs showing that CD8$^+$ CTLs induced with IL-15 respond to lower density of antigen.

FIGS. 12A-C are graphs showing cytolytic activity of CD8$^+$ CTLs expanded with high concentration of peptide (0.1 μM).

FIGS. 13A-C are graphs showing cytolytic activity of CD8$^+$ CTLs expanded with low concentration of peptide (0.001 μM).

DETAILED DESCRIPTION

Figure 1:
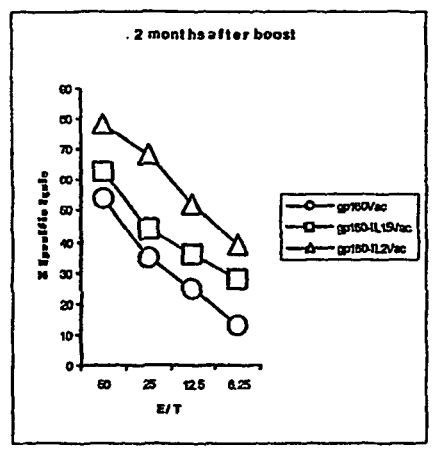
FIG. 1 is a graph showing percent specific lysis of HIV-1 gp120 peptide-pulsed cells by $CD8^+$ T cells obtained from mice 2 months after receiving recombinant vaccinia viruses according to the invention expressing both IL-15 and the gp160 antigen, both IL-2 and gp160, or gp160 alone. "E/T" refers to effector/target cell ratio.

The invention provides recombinant vaccine vectors, comprising a nucleic acid sequence encoding IL-15. Preferably, the vectors also comprise an expression unit comprising a nucleic acid sequence encoding at least one antigen operably linked to an expression control sequence; however, the antigen encoding sequence may also be provided as part of a separate nucleic acid, e.g., as part of a second recombinant vaccine vector.

The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, In *Molecular Cloning: A Laboratory Manual* (1982); *DNA Cloning: A Practical Approach*, Volumes I and II (D. N. Glover, ed., 1985); *Oligonucleotide Synthesis* (M. J. Gait, ed., 1984); Nucleic Acid Hybridization (B. D. Hames & S. J. Higgins, eds., 1985); *Transcription and Translation* (B. D. Hames & S. I. Higgins, eds., 1984); *Animal Cell Culture* (R. I. Freshney, ed., 1986); *Immobilized Cells and Enzymes* (IRL Press, 1986); B. Perbal, *A Practical Guide to Molecular Cloning* (1984). All designations of vaccinia restriction fragments, open reading frames and nucleotide positions are based on the terminology reported in Goebel, et al., *Virology* 179: 247-266, 1990; Goebel, et al., *Virology* 179: 517-563, 1990.

DEFINITIONS

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention. For example, a composition consisting essentially of IL-15 would not include other cytokines but could include non-cytokine adjuvants, antigens, therapeutic agents and the like.

As used herein, "under transcriptional control" or "operably linked" refers to expression (e.g., transcription or translation) of a polynucleotide sequence which is controlled by an appropriate juxtaposition of an expression control element and a coding sequence. In one aspect, a DNA sequence is "operatively linked" or "operably linked" to an expression control sequence when the expression control sequence controls and regulates the transcription of that DNA sequence. A construct comprising a nucleic acid sequence operably linked to an expression control sequence is referred to herein as an "expression unit" or "expression cassette".

As used herein, "an expression control sequence" refers to promoter sequences to bind RNA polymerase, enhancer sequences, respectively, and/or translation initiation sequences for ribosome binding. For example, a bacterial expression vector can include a promoter such as the lac promoter and for transcription initiation, the Shine-Dalgarno sequence and the start codon AUG (Sambrook, et al., 1989, supra). Similarly, a eukaryotic expression vector preferably includes a heterologous, homologous, or chimeric promoter for RNA polymerase II, a downstream polyadenylation signal, the start codon AUG, and a termination codon for detachment of a ribosome.

As used herein, a "nucleic acid delivery vector" is a nucleic acid molecule which can transport a polynucleotide of interest into a cell. Preferably, such a vector comprises a coding sequence operably linked to an expression control sequence.

As used herein, "nucleic acid delivery," or "nucleic acid transfer," refers to the introduction of an exogenous polynucleotide (e.g., such as an expression cassette) into a host cell, irrespective of the method used for the introduction. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome.

As used herein, a "a recombinant vaccine vector" refers to a polynucleotide to be delivered into a host cell, either in vivo, ex vivo or in vitro which comprises genomic sequences from a vaccine virus and a heterologous nucleic acid sequence (e.g., such as an expression unit for expressing IL-15 and/or an antigen). Preferably, one or more virulence-associated sequences are inactivated in the vector. A vector may be encapsulated by viral capsid proteins or may comprise naked nucleic acids or may comprise nucleic acids associated with one or more molecules for facilitating entry into a cell (e.g., such as liposomes). However, preferably, the vector is encapsulated with one or more viral capsid proteins. Examples of vaccine viruses include, but are not limited to, poxviruses as further defined below.

As used herein, "an attenuated virus" or a virus having one or more "inactivated virulence associated genes" refers to a virus that is replication deficient or which replicates less efficiently than a wild type virus in a particular host.

As used herein, the term "administering a nucleic acid to a cell" or "administering a vector to a cell" refers to infecting (e.g., in the form of a virus), transducing, transfecting, microinjecting, electroporating, or shooting the cell with the nucleic acid/vector. In some aspects, molecules are introduced into a target cell by contacting the target cell with a delivery cell (e.g., by cell fusion or by lysing the delivery cell when it is in proximity to the target cell).

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

As used herein, "IL-15 polypeptide" means a polypeptide having at least about 70%, at least about 90%, at least about 97% or about 100% homology to the wild type amino acid sequence described in Grabstein, et al., Science 264: 96, 1994 and U.S. Pat. No. 5,747,024. Variants, modified forms, biologically active fragments and fusions of IL-15 are also encompassed within the scope of this term so long as these have at least the following properties: the nucleic acids encoding the variants, modified forms, biologically active fragments and fusions of IL-15 bind to the wild-type IL-15 sequence under conditions of moderate or high stringency as defined below, and the polypeptides themselves are able to stimulate the proliferation of CTLL-2 cells (see, e.g., as described in Gillis and Smith, Nature 268:154, 1977; ATCC TIB 214).

As used herein, a "variant form of IL-15" refers to an IL-15 polypeptide which comprises conservatively substituted sequences, meaning that one or more amino acid residues are replaced by residues having similar physical and chemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Guidance concerning amino acid changes which are likely to be phenotypically silent may be found in Bowie, et al., Science 247: 1306-1310, 1990, for example. Other such conservative substitutions, for example, substitutions of regions having similar hydrophobicity characteristics, are encompassed within this definition. Conservative substitution tables providing functionally similar amino acids are well known in the art (see, e.g., Henikoff and Henikoff, Proc. Natl. Acad. Sci. USA 89: 10915-10919, 1992). Preferably, an IL-15 polypeptide retains the Asp$^{56}$ and Gln$^{156}$ residues known to be important for signal transduction. "Variants" also include forms of IL-15 which arise from alternative RNA splicing events but which nevertheless are able to function in a CTLL-2 proliferation assay and have activity substantially similar to wild type IL-15.

As used herein, "modified forms" of an IL-15 polypeptide refers to a post-translationally modified form of an IL-15 polypeptide (e.g., such as a glycosylated form or a proteolytically processed form).

As used herein, "a nucleic acid sequence encoding an IL-15 polypeptide" includes nucleic acid sequences corresponding to the wild type IL-15 nucleic acid sequence described in Grabstein, et al., Science 264: 96, 1994 and U.S. Pat. No. 5,747,024 as well as sequences which differ from the wild type IL-15 nucleic acid sequence because of degenerate substitutions and nucleic acid sequences encoding variants, modified forms, and biologically active fragments of IL-15 polypeptides. Degenerate codon substitutions can be achieved by generating sequences in which the third position of one or more selected (or all) codons is substituted with mixed-base and/or deoxyinosine residues (See, e.g., Batzer, et al., Nucleic Acid Res. 19: 5081, 1991; Ohtsuka, et al., J. Biol. Chem. 260: 2605-2608, 1985; Rossolini, et al., 1994, Mol. Cell. Probes 8: 91-98).

The term "biologically active fragment", "biologically active form", "biologically active equivalent" of and "functional derivative" of a wild-type protein, possesses a biological activity that is at least substantially equal (e.g., not significantly different from) the biological activity of the wild type protein as measured using an assay suitable for detecting the activity (e.g., at least a CTLL-2 assay in the case of a biologically active fragment of IL-15).

As used herein, the term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart.

As used herein, a "Poxvirus" includes any member of the family Poxviridae, including the subfamilies Chordopoxviridae (vertebrate poxviruses) and Entomopoxviridae (insect poxviruses). See, for example, B. Moss in Virology, ed. Fields et al., Raven Press p. 2080 (1990). The chordopoxviruses comprise the following genera: Orthopoxvirus (e.g., vaccinia); Avipoxvirus (e.g., fowlpox); Capripoxvirus (e.g., sheeppox) Leporipoxvirus (e.g., rabbit (Shope) fibroma, myxoma); and Suipoxvirus (e.g., swinepox).

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism.

As used herein, a "patient" is a vertebrate, preferably a mammal, more preferably a human. Mammals include, but are not limited to, murines, non-human primates, humans, farm animals, sport animals, pets, and feral or wild animals.

The terms "cancer," "neoplasm," and "tumor," are used interchangeably and in either the singular or plural form, refer to cells that have undergone a malignant transformation that makes them pathological to the host organism. Primary cancer cells transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see *Martin Remington's Pharm. Sci.*, 15th Ed. (Mack Publ. Co., Easton (1975).

The term "antigen source" as used herein covers any substance that will elicit an innate or adaptive immune response. An antigen source may require processing (e.g., such as proteolysis) to produce an antigen. An antigen source may be a polypeptide/protein, peptide, microorganism, tissue, oligo- or polysaccharide, nucleic acid (encoding an antigen or a polypeptide/protein comprising an antigen or itself serving as the antigen).

As used herein, the terms "antigen", "antigenic determinant" or "epitope" are used synonymously to refer to a short peptide sequence or oligosaccharide, that is specifically recognized or specifically bound by a component of the immune system. Generally, antigens are recognized in the context of an MHC/HLA molecule to which they are bound on an antigen presenting cell. Two antigens "correspond" to each other if they can be specifically bound by the same antibody, B cell, or T cell, and binding of the epitope to the antibody, B cell, or T cell substantially prevents binding by the other epitope (e.g., binding of a first epitope in the presence of a second epitope is less than about 30%, preferably, less than about 20%, and more preferably, less than about 10%, 5%, 1%, or about 0.1% of binding observed in the absence of the second epitope);

As used herein, a "vaccine composition" comprises a vaccine vector encoding and IL-15 polypeptide and at least one antigen source. The antigen source may comprise a nucleic acid encoding an antigen included as part of the vaccine vector or which is provided as a separate nucleic acid molecule. The components of a vaccine composition may be administered together or sequentially.

As used herein, a "vaccine" refers to a material that contains or encodes an antigen which will provide active immunity to material comprising the antigen, but will not cause disease.

As used herein, a "subunit vaccine" refers to a vaccine that contains only part of the virus or other microorganism, e.g., including viral or microbial polypeptides or nucleic acids encoding such polypeptides capable of eliciting an immune response.

As used herein, a "therapeutic vaccine" is a vaccine designed to boost the immune response to an antigen in a person already exposed to the antigen.

As used herein, a "therapeutically effective amount" refers to an amount sufficient to prevent, correct and/or normalize an abnormal physiological response. In one aspect, a "therapeutically effective amount" is an amount sufficient to reduce by at least about 30 percent, more preferably by at least 50 percent, most preferably by at least 90 percent, a clinically significant feature of pathology, such as for example, e.g., suppression of CD4 cells (i.e., resulting in an increase in CD4 cells by a least 30%, etc), decrease in viral load; decrease in size of a tumor mass, and the like. Preferably, a "therapeutically effective amount of a vaccine composition" enhances a beneficial immune response to a vaccine antigen by at least about 30%, more preferably by at least about 50% or at least about 90%, i.e., increasing CTL responses against the antigen, increasing secretion of $\gamma$-IFN by $CD8^+$ T, increasing production of antibodies specific for a vaccine antigen and increasing the duration of these responses after administration of a vaccine composition.

As used herein, a immune response with "increased duration" refers to a significant response observed at at least about 4 months, about 6 months, about 8 months, about 10 months, about 12 months, about 16 months, about 18 months, or at least about 20 months after initial administration of an antigen.

An "antibody" is any immunoglobulin, including antibodies and fragments thereof, that binds a specific antigen. The term encompasses polyclonal, monoclonal, and chimeric antibodies (e.g., bispecific antibodies). An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', $F(ab')_2$ and F(v) portions, which portions are preferred for use in the therapeutic methods described herein.

As used herein, the term "immune effector cells" refers to cells capable of binding an antigen and which mediate an immune response. These cells include, but are not limited to, T cells, B cells, monocytes, macrophages, dendritic cells, NK cells and cytotoxic T lymphocytes (CTLs), for example CTL lines, CTL clones, and CTLs from tumor, inflammatory, or other infiltrates.

As used herein, the term "viral infection" describes a disease state in which a virus invades healthy cells, uses the cell's reproductive machinery to multiply or replicate and ultimately lyse the cell resulting in cell death, release of viral particles and the infection of other cells by the newly produced progeny viruses. A "non-productive infection", i.e., by a vaccine virus vector is an infection in which the vector is introduced into a cell but does not replicate within the cell, either because of inactivation of virulence associated gene(s) or because of a restricted host-range.

As used herein, the term "treating or preventing viral infections" means to inhibit the replication of the particular virus, to inhibit viral transmission, or to prevent the virus from establishing itself in its host, and to ameliorate or alleviate the symptoms of the disease caused by the viral infection.

As used herein, an "adjuvant" refers to a substance that enhances, augments or potentiates the host's immune response to a vaccine antigen.

The term "immunogenicity" means relative effectiveness of an immunogen or antigen to induce an immune response.

As used herein, "baseline" refers to the time point just before administration of a vaccine when starting measurements are taken.

As used herein, a "booster" refers to a second or later vaccine dose given after the primary dose(s) to increase the immune response to the original vaccine antigen(s). The vaccine given as the booster dose may or may not be the same as the primary vaccine.

As used herein, "challenge" refers to the deliberate exposure of a host animal to a vaccine antigen.

As used herein, a "clade" refers to a group of related HIV isolates classified according to their degree of genetic similarity (e.g., such as measured by the similarity of their envelope proteins). There are currently two groups of HIV-1 isolates, M and O. The M group consists of at least nine clades, A through I. Group O may consist of a similar number of clades. Clade B is commonly found in North America and Europe, and includes isolates LAI b, MN, and SF-2.

As used herein, "seroconversion" refers to the development of antibodies to a particular antigen.

As used herein, "immunity" refers to natural or acquired resistance provided by the immune system to a specific disease. Immunity may be partial or complete, specific or non-specific, long-lasting or temporary.

As used herein, "sterilizing immunity" refers to an immune response that completely prevents the establishment of an infection.

As used herein, a "memory cell" refers to a subset of T cells and B cells that have been exposed to specific antigens and can then proliferate (recognize the antigen and divide) more readily when the immune system re-encounters the same antigens.

Recombinant Vectors

The invention provides a vaccine vector comprising a nucleic acid sequence encoding an IL-15 polypeptide for inducing or enhancing an immune response to an antigen. Preferably, the vaccine vector is a poxvirus vector such as a vaccinia vector. The invention can generally be implemented to produce and/or enhance a cellular or humoral immune response against a selected antigen ("a vaccine antigen").

The cloning and sequencing of IL-15 is disclosed in Grabstein, et al., *Science* 264: 96, 1994 and in U.S. Pat. No. 5,747,024. As used herein, an "IL-15 nucleic acid" hybridizes to the wild-type IL-15 sequence under conditions of moderate or high stringency and is able to stimulate the proliferation of CTLL-2 cells (Gillis and Smith, *Nature* 268: 154, 1977; ATCC TIB 214).

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

Preferably, the IL-15 nucleic acid sequence encodes an IL-15 polypeptide which comprises at least about 70% homology to the wild type IL-15 polypeptide and more preferably, comprises at least about 90% homology or about 100% homology to the wild type IL-15 polypeptide.

Percent identity and similarity between two sequences (nucleic acid or polypeptide) can be determined using a mathematical algorithm (see, e.g., *Computational Molecular Biology*, Lesk, A. M., ed., Oxford University Press, New York, 1988; *Biocomputing: Informatics and Genome Projects*, Smith, D. W., ed., Academic Press, New York, 1993; Computer Analysis of Sequence Data, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

To determine the percent identity of two amino acid sequences or of two nucleic acid sequences, the sequences are aligned for optimal comparison purposes (e.g., gaps are introduced in one or both of a first and a second amino acid or nucleic acid sequence for optimal alignment and non-homologous sequences can be disregarded for comparison purposes). The percent identity between the two sequences is a function of the number of identical positions shared by the sequences, taking into account the number of gaps, and the length of each gap which need to be introduced for optimal alignment of the two sequences. The amino acid residues or nucleotides at corresponding amino acid positions or nucleotide positions, respectively, are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

A "comparison window" refers to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art.

For example, the percent identity between two polypeptide sequences can be determined using the Needleman and Wunsch algorithm (J. Mol. Biol. (48): 444-453, 1970) which is part of the GAP program in the GCG software package (available at http://www.gcg.com), by the local homology algorithm of Smith & Waterman (Adv. Appl. Math. 2: 482, 1981), by the search for similarity methods of Pearson & Lipman (Proc. Natl. Acad. Sci. USA 85: 2444, 1988) and Altschul, et al. (Nucleic Acids Res. 25(17): 3389-3402, 1997), by computerized implementations of these algorithms (GAP, BESTFIT, FASTA, and BLAST in the Wisconsin Genetics Software Package (available from, Genetics Computer Group, 575 Science Dr., Madison, Wis.), or by manual alignment and visual inspection (see, e.g., Ausubel et al., supra).

Gap parameters can be modified to suit a user's needs. For example, when employing the GCG software package, a NWSgapdna.CMP matrix and a gap weight of 40, 50, 60, 70, or 80 and a length weight of 1, 2, 3, 4, 5, or 6 can be used. Exemplary gap weights using a Blossom 62 matrix or a PAM250 matrix, are 16, 14, 12, 10, 8, 6, or 4, while exemplary length weights are 1, 2, 3, 4, 5, or 6. The GCG software package can be used to determine percent identity between nucleic acid sequences. The percent identity between two amino acid or nucleotide sequences also can be determined using the algorithm of E. Myers and W. Miller (CABIOS 4: 11-17, 1989) which has been incorporated into the ALIGN program (version 2.0), using a PAM120 weight residue table, a gap length penalty of 12 and a gap penalty of 4.

In one aspect of the invention, a human cDNA of IL-15 encodes a 162-amino acid precursor, which contains a 316 bp 5' noncoding region and a 489 bp open reading frame (including the stop codon) and a 400 bp 3' noncoding region (see, e.g., Grabstein, et al., Science 264: 965, 1994). Recombinant vectors can include the full length cDNA or portions comprising the coding region or biologically active fragments thereof (e.g., lacking one or more of the 5' noncoding region and 3; noncoding region). Recombinant vectors can also include sequences corresponding to sequences encoding the 114 amino acid processed form of IL-15. Such sequences may be fused to non-IL-15 secretory sequences, for example, the signal sequence of an immunoglobulin kappa light chain.

Preferably, recombinant IL-15 polypeptides expressed in vectors according to the invention have substantially the same activity as wild type IL-15, as determined in a CTLL-2 assay. See, Grabstein, et al., 1994, supra. Briefly, CTLL-2 cells (about $2 \times 10^4$-$10^6$) are added to serial dilutions of recombinant IL-15 polypeptides in a 96-well plate or other suitable container and incubated at 37° C. and 5%, $CO_2$ for 3 days. Subsequently, 0.5 µCi $^3$H-thymidine is added to the mixture. Thymidine is incorporated only if the cells proliferate. After an overnight incubation, cells are harvested (e.g., on glass fiber filters) and radioactivity is measured using a suitable detector such as a beta counter (e.g., such as the Matrix 96 beta counter, available from Packard Instrument Company, Meridien, Conn.). The activity of recombinant IL-15 in the sample is determined from a standard curve generated using known amounts of IL-15. Recombinant human IL-15 for use as a standard can be purchased commercially (e.g., from PeproTech, London, UK). A recombinant IL-15 polypeptide according to the invention preferably shows less than about 20% difference from the standard curve, more preferably, less than about 10% difference, and still more preferably, less than about 5% difference. In one aspect, the recombinant IL-15 polypeptide has a specific activity of about $5 \times 10^5$-$2 \times 10^6$ U/mg according to the manufacturer. While a thymidine incorporation assay is described above, it should be obvious to those of skill in the art that any suitable assay for measuring cell proliferation may be used and is encompassed within the scope of the instant invention.

Preferably, IL-15 nucleic acids encode IL-15 polypeptides which bind with specificity to the α subunit of the IL-15 receptor (IL-15R) and which can transduce a signal through either, or both, the β- or γ-subunits of the IL-15 receptor complex. In a further aspect, recombinant IL-15 polypeptides according to the invention act as chemoattractant factors for human peripheral blood T lymphocytes, as assayed by determining one or more of: induction of polarization, invasion of collagen gels and redistribution of adhesion receptors (see, e.g., as described in Wilkinson and Liew, *J Exp Med.* 181(3): 1255-9, 1995; Nieto, et al., *Eur. J Immunol* 26(6): 1302-7, 1996).

Administration of recombinant IL-15-expressing vaccine vectors according to the invention results in the production of an expanded population of memory cells which are primed to produce a secondary response upon re-exposure to the antigen. This effect can be monitored by the ability of such cells to expand rapidly in the presence of the vaccine antigen presented by antigen presenting cells (APCs), or their ability to display a rapid antigen-specific cytolytic response even after the primary exposure to the antigen.

Cell death can be monitored by assays known in the art, for example, by counting trypan-blue dye excluding cells in a hemocytometer. Apoptosis can be analyzed by addition of propidium iodide (PI) (ICN) to harvested cells and determining the percentage of cells taking up PI by flow cytometry. The percentage of apoptotic cells can be determined by forward scatter analysis as is known in the art and correlated with PI uptake. Preferably, recombinant polypeptides protect CD8$^+$ T cells from cell death, causing less than about 20%, less than about 10%, and less than about 5% change in the number of cells at concentrations of recombinant IL-15 of about 0.1 ng/ml or higher, and less than 20%, less than 10% and preferably, less than about 5% increase in the number of apoptotic cells in the population.

The ability of recombinant IL-15 polypeptides to enhance a memory response can be evaluated by infecting mice with vaccine vectors according to the invention in the presence of a vaccine antigen or a vaccine antigen-encoding sequence. Mice are sacrificed at various days after antigen exposure and lymph node cells from naïve mice, treated mice, or mice treated with buffer, are isolated and restimulated with vaccine antigen or an irrelevant antigen (e.g., such as hen egg lysozyme or an influenza antigen). Cell proliferation is monitored using methods routine in the art (e.g., by measuring the incorporation of $^3$H-thymidine. A significant increase in proliferation in memory cells as compared to buffer treated or naïve mice (as determined using statistical methods well known in the art) is taken as an indication of an enhanced memory response. Preferably, recombinant IL-15 expressing viral vectors are capable of producing an at least about 25%, at least about 50%, or at least about 100% increase in proliferation. Additionally, or alternatively, the responses of memory cells are taken as indicia of biologically active IL-15. Preferably, such responses include cytolysis by vaccine-antigen specific CD8+ T cells and/or γ-IFN production by such cells. Preferably, administration of biologically active IL-15 enhances the duration and magnitude of responses by CD8$^+$ T cells.

As discussed above, preferred vaccine vectors include poxviruses. The large genome size of these viruses permits the engineering of vectors capable of accepting at least 25,000 base pairs of foreign DNA (Smith, et al., *Gene* 25: 21, 1983). Additionally, poxviruses can infect most eukaryotic cell types and do not require specific receptors for entry into a cell. Unlike other DNA viruses, poxviruses replicate exclusively in the cytoplasm of infected cells, reducing the possibility of genetic exchange of recombinant viral DNA with the host chromosome and allowing heterologous genes to be expressed independent of host cell regulation.

A poxvirus vector may be obtained from any member of the poxviridae, in particular, a vaccinia virus or an avipox virus (e.g., such as canarypox, fowlpox, etc.) provides a suitable sequences for vaccine vectors.

In one aspect, the poxviral vector is a vaccinia virus vector. Vaccinia virus has demonstrated physical and genetic stability under field conditions, reducing problems and expense in transport and storage. Recombinant vaccinia virus vectors have been shown to confer cellular and humoral immunity against foreign gene products and to protect against infectious diseases in several animal models. Further, recombinant vaccinia viruses have also been used in clinical trials to express the gp160 envelope gene of HIV (see, e.g., Cooney, *The Lancet* 337: 567-572, 1991; Graham, et al., *J. of Infectious Dis.* 166: 244-252, 1992; Estin, et al., *Proc. Natl. Acad. Sci. USA* 85: 1052-1056, 1988) and are thus clinically accepted.

Suitable vaccinia viruses include, but are not limited to, the Copenhagen (VC-2) strain (Goebel, et al., *Virol* 179: 247-266, 1990; Johnson, et al., *Virol.* 196: 381-401, 1993), modified Copenhagen strain (NYVAC) (U.S. Pat. No. 6,265,189), the WYETH strain and the modified Ankara (MVA) strain (Antoine, et al., *Virol.* 244: 365-396, 1998). However, although the examples below are directed to vaccinia viruses, other poxviruses suitable for use as vaccines may be substituted and are also encompassed within the scope of the invention. For example, fowlpox strains such as ALVAC and TROVAC vectors also provide desirable properties and are highly attenuated (See, e.g., U.S. Pat. No. 6,265,189, reviewed by Tartaglia et al., In *AIDS Research Reviews*, Koff, et al., eds., Vol. 3, Marcel Dekker, N.Y., 1993; Tartaglia et al., 1990, *Reviews in Immunology* 10: 13-30, 1990).

Methods and conditions for constructing recombinant poxvirus virus vectors, such as vaccinia virus vectors, are known in the art (see, e.g., Piccini, et al., *Methods of Enzymology* 153: 545-563, 1987; U.S. Pat. No. 4,769,330; U.S. Pat. No. 4,722,848; U.S. Pat. No. 4,769,330; U.S. Pat. No. 4,603,112; U.S. Pat. No. 5,110,587; U.S. Pat. No. 5,174,993; EP 83 286; EP 206 920; Mayr et al., *Infection* 3: 6-14, 1975; Sutter and Moss, *Proc. Natl. Acad. Sci. USA* 89: 10847-10851, 1992). The preparation of fowlpox virus is described in WO 96/11279, for example.

A vaccine vector is generally prepared as follows. In one aspect, a donor plasmid comprising a nucleic acid sequence encoding IL-15 is constructed, amplified by growth in *E. coli* and isolated by conventional procedures. The donor plasmid comprises a nucleic acid sequence homologous to vaccinia virus sequences. The nucleic acid encoding IL-15 is operably linked to an expression control element. Preferably, the expression control element comprises viral regulatory elements, including upstream promoter sequences and, where necessary, RNA processing signals. The expression control sequences may be from a vaccinia virus, or other poxvirus (see, e.g., Mackett, et al., *J Virol,* 49: 857, 1982), and is operably linked to the nucleic acid sequence encoding the IL-15 polypeptide. The choice of promoter determines both the time (e.g., early or late) and level of expression of the IL-15 sequence.

The expression unit comprising the expression control sequence and IL-15 sequence is flanked on both ends by DNA homologous to a vaccinia virus DNA sequence being targeted as a recombination site. Preferably, the flanking sequences correspond to a nonessential locus in the vaccinia viral genome. The resulting plasmid construct is then amplified by replication in *E. coli* or other suitable host and isolated using methods routine in the art (see, e.g., Maniatis, T., Fritsch, E. F., and Sambrook, J., In *Molecular Cloning: A Laboratory Manual* (Cold Spring Harbor Laboratory, Cold Spring Harbor, N.Y.) (1989)).

A suitable cell culture (e.g., chicken embryo fibroblasts, CV-1 cells, BHK-21 cells, 143B tk-cells, vero cells, lung cells, etc.) is transfected with the donor plasmid along with recipient vaccinia virus sequences to select for recombinants that comprise both donor and recipient sequences. Transfection may be facilitated by providing one or more molecules for facilitating entry of a nucleic acid into a cell. Suitable delivery vehicles include, but are not limited to: liposomal formulations, polypeptides; polysaccharides; lipopolysaccharides, cationic molecules, cell delivery vehicles, vehicles for facilitating electroporation, and the like.

Suitable recipient sequences are selected which will result in the production of a recombinant virus that can induce and/or enhance a protective immune response and which lacks any significant pathogenic properties. Therefore, in one preferred aspect, the recipient sequence comprises one or more genes which are non-essential for growth of the virus in tissue culture and whose deletion or inactivation reduces virulence in a host organism, such as mammal (e.g., such as a mouse or a human being).

Virulence associated sequences include, for example, the thymidine kinase (TK) gene; hemagglutinin; 13.8 kD secreted protein, ribonucleotide reductase genes; host range genes; hemorrhagic gene, and A type inclusion body region. See, e.g., Hruby et al., *J. Virol.* 43: 403-409, 1982; Weir, et al., *Proc. Natl. Acad. Sci. USA* 80: 3411-3415, 1983; Flexner, et al., *Nature* 330: 259, 1987; Buller, et al., *Nature* 317: 813, 1985; Buller, et al., *J. Virol.* 62: 866, 1988; Shida et al., *J. Virol* 62: 4474, 1988); Kotwal, et al., *Virology* 171: 579, 1989; Child, et al., *Virology* 174: 626, 1990). Inactivated virulence associated sequences can comprise whole or partially deleted gene sequences, substitutions, rearrangements, insertions, combinations thereof and the like. Mutations can be engineered or selected for. For example, attenuated viral strains can be selected for by repeated passages in a suitable vertebrate host cell (e.g., such as chicken embryonated eggs and/or chicken fibroblasts) and subsequent plaque purification to identify plaques which are smaller, replicate more slowly, or which display other indications of complete or partial attenuation. Preferably, a poxvirus vector according to the invention is replication incompetent and incapable of spreading beyond initially infected cells or is attenuated.

Host restricted viruses such as avipox viruses can also be used as these are nonvirulent in mammals, such as humans.

Recombination between a homologous vaccinia virus sequence in the donor plasmid and the viral genome results in production of vaccinia vector that comprises IL-15-encoding sequences.

Recombinants can be detected by including reporter gene sequences in the donor plasmid and screening for recombinant viruses that carry these sequences. For example, donor plasmids that contain the *E. coli* β-galactosidase gene provide a method of distinguishing recombinant from parental viruses (Chakrabarti, et al., *Mol. Cell. Biol.* 5: 3403, 1985). Plaques formed by such recombinants can be positively identified by the blue color that forms upon addition of an appropriate indicator. Alternatively, or additionally, the recipient sequence comprises a reporter sequence and recombinants are detected by loss of function of the reporter sequence (i.e., resulting from insertion of donor sequences into the recipient sequence). In one aspect, the recipient reporter sequence is a virulence associated gene. For example, insertion into the thymidine kinase gene will result in recombinants that grow in the presence of bromo-deoxyuridine (BrdU) in thymidine kinase negative 143B osteosarcoma cells.

However, in another aspect, the recipient reporter sequence is a heterologous sequence (e.g., such as β-galactosidase or guanine-phosphoribosyl transferase). Additional strategies for generating recombinant vaccinia virus are described in Scheiflinger, et al., *Proc. Natl. Acad. Sci. USA* 89: 9977-9981, 1992; Merchlinsky and Moss, *Virology* 190: 522-526, 1992, for example.

Viral particles can be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or by ultracentrifugation on cesium chloride or sucrose gradients).

Vectors according to the invention may additionally comprise a detectable and/or selectable marker to verify that the vector has been successfully introduced in a target cell. These markers can encode an activity, such as, but not limited to, production of an RNA, peptide, or protein, or can provide a binding site for RNA, peptides, proteins, inorganic and organic compounds or compositions and the like. In some cases the reporter sequence provided by the donor plasmid is used as the marker to verify introduction into a target cell.

Examples of detectable/selectable markers genes include, but are not limited to: nucleic acid sequences which encode: products providing resistance to otherwise toxic compounds (e.g., such as antibiotics); products which are otherwise lacking in a recipient cell (e.g., tRNA genes, auxotrophic markers, and the like); products which suppress the activity of a gene product; enzymes (e.g., such as β-galactosidase or guanine-phosphoribosyl transferase), fluorescent proteins (GFP, CFP, YFG, BFP, RFP, EGFP, EYFP, EBFP, dsRed, mutated, modified, or enhanced forms thereof, and the like); cell surface proteins (i.e., which can be detected by an immunoassay); antisense oligonucleotides; and the like.

The marker gene can be used as a marker to confirm successful IL-15 gene transfer by the vaccine vector and/or to isolate recombinants expressing IL-15.

In one aspect, the vaccine vector comprises viral capsid molecules to facilitate entry of the vaccine vector into a cell. Additionally, viral capsid molecules may be engineered to include targeting moieties to facilitate targeting and/or selective entry into specific cell types. Suitable targeting molecules, include, but are not limited to: chemical conjugates, lipids, glycolipids, hormones, sugars, polymers (e.g. PEG, polylysine, PEI and the like), peptides, polypeptides (see, e.g., WO 94/40958), vitamins, lectins, antibodies and fragments thereof. Preferably, such targeting molecules recognize and bind to cell-specific markers of antigen presenting cells, such as dendritic cells (e.g., such as CD44) or cancer cells.

Antigen Encoding Sequences

An antigenic source can be administered in the form of polypeptides or peptides conjugated to a carrier or can be administered in the form of nucleic acid sequences encoding the antigen. Preferably, antigen source will contain regions that stimulate one or more response of the immune system: e.g., including, but not limited to: immunoglobulin responses, MHC/HLA I responses, MHC/HLA class II responses, NK responses and the like. In the case of MHC/HLA class II mediated responses, the antigen source will generally contain peptide segments that can be released by lysosomal enzymes within a cell and, when released, correspond to MHC/HLA class II epitopes.

Synthetic antigens and altered antigens also can be used in the methods described herein. Synthetic antigens have modified amino acid sequences relative to their natural counterparts (in this embodiment, the antigen is provided in the form of a peptide rather than a nucleic acid encoding the peptide). Also encompassed within the scope of the invention multimers (concatamers) of the antigen, optionally including intervening amino acid sequences or linkers. Where a plurality of antigens are encoded by an antigen expression unit forming a multivalent antigen expression unit, the antigens may be the same or different.

In one aspect, a multivalent antigen expression unit comprises at least one CTL epitope, at least one helper epitope, and at least one B cell epitope from the same or different antigen source. The different epitopes may be from the same or different proteins. For example, a plurality of antigen sequences may be a combination of antigens from at least two strains of infectious organisms (e.g., from HIV and *Pneumocystic cariini*), from different polypeptides encoded by the genome of a single infectious organism, or from a single polypeptide, e.g., different antigenic regions or representing variants of the same antigenic sequence. In the latter embodiment, variants of the same antigenic sequence may be used to induce or enhance an immune response against a particularly mutable peptide sequence (e.g., within an infectious organism).

Also included within the scope of the invention are antigenic peptides that are differentially modified during or after translation, e.g., by phosphorylation, glycosylation, crosslinking, acylation, proteolytic cleavage, linkage to an antibody molecule, membrane molecule or other ligand (see, e.g., Ferguson et al., *Ann. Rev. Biochem.* 57: 285-320, 1998).

Suitable antigens include, but are not limited to: cancer/tumor antigens, autoantigens (e.g., such as antigens recognized in transplant rejection); allergens; antigens associated with hypersensitivity; prion antigens; viral antigens; bacterial antigens; antigens from protozoa or fungi; and parasitic antigens, including especially proteins found in the cell walls or cell membranes of these organisms.

In particular, suitable antigens are antigens encoded by the genomes of organisms associated with rabies (e.g., GenBank Accession No. M34678), malaria (Shetty, *Lancet Infect Dis.* 2(11): 648, 2002), parasitic infections (e.g., such as schistosomiasis), hantavirus (Meissner, et al., *Virus Res.* 89(1): 131, 2002; Padula, et al., *J. Gen Virol.* 83(Pt 2: 2117-22, 2002; Hoffacker, et al., *Nucleic Acids Res.* 26(16): 3825-36, 1998); yellow fever (Pugachev, et al., *Vaccine* 20(7-8): 996-9, 2002); West Nile fever (Lanciotti, et al., *Virology* 298(1): 96-105, 2002); measles (Crowley, et al., *Intervirology* 28(2): 65-77, 1987); mumps (Jin, et al., *Virus Res.* 70(1-2): 75-83, 2000); rubella (Iominguez, et al., *Virology* 177(1): 225-38, 1990); poliomyelitis (see, e.g., Kinnunen, et al., *J Gen Virol.* 72 (Pt 10): 2483-9, 1991); smallpox (Massung, et al., *Virology* 201 (2): 215-40, 1994; Mayr, et al., *Zentralbl. Bakteriol [B]*. 167(5-6): 375-90, 1978; Aguado, et al., *J Gen Virol.* 73(Pt 11): 2887-902, 1992; Shchelkunov, et al., *Virus Res.* 36(1): 107-18, 1995); anthrax; Ebola (Sanchez, et al., *Virus Res.* 29(3): 215-40, 1993); equine encephalitis (Kinney, et al., *Virology* 170(1):19-30, 1989); Rift valley fever (Muller, et al., Nucleic Acids Res. 19(19): 5433, 1991); cat scratch fever (see, e.g., Renesto, et al., *Res Microbiol.* 151(10): 831-6, 2000); viral meningitis; Marburg virus (Sanchez, et al., 1993, supra); hepatitis A, B, C, D, and E (see, generally GenBank); Japanese encephalitis (e.g., GenBank Accession No. E07883); dengue (e.g., GenBank Accession No. M24444); plague (Parkhill, et al., *Nature* 413(6855): 523-7, 2001), tularemia (Karlsson, et al., *Microb. Comp. Genomics* 5(1): 25-39, 2000); and diseases caused by other pathogenic organisms including Chlamydial and Rickettsial agents.

Particularly preferred antigens are virally-encoded proteins encoded by the genome of viruses pathogenic to man or domestic animals. Non-limiting examples include peptides from the influenza nucleoprotein composed of residues 365-80 (NP365-80), NP50-63, and NP147-58 and peptides from influenza hemagglutinin HA202-21 and HA523-45, defined previously in class I restricted cytotoxicity assays (Perkins et al., 1989, *J. Exp. Med.* 170: 279-289). Relevant protozoan antigens include peptides representing epitopes displayed by the malarial parasite *Plasmodium falciparum* have been described (see, e.g., U.S. Pat. No. 5,609,872). Papilloma virus core antigen, HCV structural and non-structural proteins; and CMV structural and non-structural proteins, Ebola GP1 or GP2 protein (see, e.g., Feldmann, et al., *Arch Virol Suppl.* 15: 159-69, 1999; Sanchez, et al., *J. Virol* 72(8: 6442-7, 1998; Volchkov, V. E., et al., *FEBS Lett* 305(3): 181-4, 1992), or nucleocapsid protein (Vanderzanden, et al., *Virology,* 246(1): 134-44, 1998) also provide sources of antigens. In another aspect, antigens are derived from a respiratory syncytial virus (RSV). For example, the RSV viral antigen may be the glycoprotein (G-protein) or the fusion protein (F-protein). In a further aspect, antigens are derived from the herpes simplex virus (HSV), such as HSV-1 and HSV-2. For example, the HSV viral antigen may be the glycoprotein D from HSV-2.

In one preferred aspect, a rabies virus provides a source of antigen. Currently, multivalent rabies antigens demonstrate "efficacy interference" in dogs, namely a failure of one or more antigens (canine distemper virus antigens, canine adenovirus antigens, canine coronavirus antigens, canine parainfluenza antigens, canine parvovirus antigens, and Leptospira bacterin antigens), when used in combination with a rabies antigen, to maintain a satisfactory immune response. See, e.g., U.S. Pat. No. 5,843,456. Therefore, the recombinant vaccinia viruses according to the invention are particularly useful because of their ability to maintain a significant long-term immune response (greater than a year).

Thus, in one preferred aspect of the invention, vaccine compositions according to the invention comprise a source of rabies antigen (i.e., a nucleic acid encoding a rabies antigen) and a recombinant IL-15 expressing sequence. Suitable sources of rabies antigens include, but are not limited to glycoprotein G. See, e.g., Wiktor, et al., *J. Imunol.* 110: 269-276, 1973. Vectors comprising encoding rabies antigens are described in U.S. Pat. No. 6,210,663, for example. Such compositions may include additional antigen sources (e.g., including different portions of glycoprotein G) to provide multivalent vaccines as described above.

In aspect, a preferred antigen is a small pox antigen. In this embodiment, a vaccinia virus itself provides a suitable source of antigens because of its close antigenic and genetic relatedness to small pox strains. Currently, vaccinia vaccines, such as the Wyeth strain, can give rise to adverse effects in a small number of vaccines, including eczema vaccinatum and encephalitis. During the smallpox eradication era, about 1250 in every million people vaccinated suffered these side effects and about one in a million died. Young children under two years of age were especially vulnerable. The numbers of deaths would likely increase if a smallpox eradication program commenced again because of the higher percentage of immunosuppressed individuals in the population (e.g., individuals with AIDS or taking immunosuppressive drugs). Further, the prevalence of eczema in the general population has risen for unknown reasons (see, *Science* 296: 1592-1595, 2002; Smith, et al., *Nature Reviews/Immunology* 2: 521-526, 2002). Because of these reasons, there is a real need for a safer vaccine and recombinant-IL-15 expressing vaccines generated from strains such as Wyeth and MVA can meet this need in at least three ways. First, by incorporating IL-15 expressing sequences into the vaccine, both humoral and cell-mediated immune responses will be augmented. Second, insertional inactivation by IL-15 sequences of a virulence associated gene such as the hemagluttinin will result in attenuation of the virus. Third, expressed IL-15 itself will lead to reduction in virulence due to activation of NK cells, as well as enhanced interferon gamma and chemokine production.

In another particularly preferred aspect, an antigen is selected which is associated with a chronic pathology, such as AIDS (e.g., GenBank Accession No. U18552). The causative agent of AIDS is the human immunodeficiency virus (HIV), a pathogenic retrovirus (see, e.g., Barre-Sinossi, et al., *Science* 220: 868-870, 1983; Gallo, et al., *Science* 224: 500-503, 1984). There are at least two distinct types of HIV: HIV-1 (Barre-Sinossi, et al., 1983, supra; Gallo, et al., 1984, supra) and HIV-2 (Clavel, et al., *Science* 223: 343-346, 1986; Guyader, et al., *Nature* 326: 662-669, 1987). Types of HIV are further divisible into strains, isolates and clades.

Therefore, preferably, in one aspect according to the invention, the antigen is from a pathogenic virus which comprises HIV, including various types of HIV (e.g., HIV-1 and HIV-2), strains (e.g., strain BH10 and pNL4-3 of HIV-1), isolates, clades (e.g., lade A, B, C, D, E, F, and G of group M) and the like.

The viral antigen may be an HIV envelope protein, such as HIV envelope protein Env, either full-length (gp160), truncated (e.g., gp120 and gp41), and can be modified with insertions, deletions or substitutions. The HIV envelope proteins have been shown to be the major antigens for anti-HIV antibodies present in AIDS patients (see, e.g., Barin, et al., *Science* 228: 1094-1096, 1985). The amino acid and RNA sequences encoding HIV envelope from a number of HIV strains are known. See Myers, G. et al., *Human Retroviruses and AIDS: A compilation and analysis of nucleic acid and amino acid sequences*, Los Alamos National Laboratory, Los Alamos, N.M. (1992).

In one preferred aspect, an epitope is selected from the V3 region of the gp120 polypeptide, the V1-V2 region, the CD4 binding site, the C4 region, a CCR binding region, such as the binding region for CCR5 or CCR3. The location of neutralizing epitopes in the V3 domain is well known. It has been found that neutralizing epitopes in the V2 and C4 domains are located between residues 163 and 200 and between about 420 and 440, respectively. In addition, residues for antibody binding also include residues 171, 174, 177, 181, 183, 187, 188 in the V2 domain and residues 429 and 432 in the C4 domains. See, e.g., Berman, et al. *Virology* 265: 1-9, 1999; and Berman, *AIDS Res. Human Retroviruses* 15: 115-132.

In another embodiment, the HIV antigen expressed by the recombinant virus of the present invention is a modified Env protein that contains deletions and/or mutations in the glycosylation sites. The gp120 of HIV-1 contains 24 potential sites for N-linked glycosylation (Asn-X-Ser/Thr). Approximately 13 of the 24 glycosylation sites are conserved in the different viral isolates. Analysis of HIV-1 Env proteins has demonstrated that 17 of 24 potential glycosylation sites are modified with carbohydrate side chains and therefore, because of the extensive glycosylation of Env gp proteins, very few regions of the peptide backbone of gp120 may protrude from the carbohydrate mass. Some of the glycosylation sites have been found in non-neutralizing epitopes that dilute the immunity against true neutralizing epitopes or serve as decoy epitopes. Thus, deletion or mutation of these glycosylation sites may enhance immunity of the antigen by unmasking the true neutralizing epitopes. See, e.g., Mizuochi, et al. *J. Biol. Chem.* 265: 8519-8524, 1990; and Leonard et al., *J. Biol. Chem.* 265:10373-10382, 1990.

Other viral antigens include either full length wild type, modified, or protease-processed products or fragments, including, but not limited to: capsid proteins such as HIV (gp17); or HIV regulatory proteins, such as Tat, Vif, Vpr, Nef, and Rev.

Another preferred antigen source is the HIV matrix protein, or gag. Gag (gp24) is relatively conserved among diverse HIV strains and subtypes and broad cross-class anti-Gag CTL responses have been demonstrated in HIV-infected patents. Studies of exposed but sero-negative subjects indicate that Gag-specific CTL may be involved in protection against the establishment of a persistent HIV infection. Additionally, Gag-specific CD8[+] cytotoxic T lymphocytes are important in controlling virus load during acute infection as well as during the asymptomatic stages of the infection. Multiple discrete Gag epitopes have been described and shown to mediate cytotoxic activities. Moreover, levels of p24-specific CTL proliferative responses of infected untreated persons have been positively correlated with levels of Gag-specific CTL and negatively correlated with levels of plasma HIV-1 RNA. See, e.g., U.S. Published Application No. 20020160430.

Other characterized HV epitopes are included in the HIV Molecular Immunology Database published yearly by Los Alamos. See, e.g., *HIV Molecular Immunology* 2001, Editors: Bette T. M. Korber, Christian Brander, Barton F. Haynes, Richard Koup, Carla Kuiken, John P. Moore, Bruce D. Walker, and David I. Watkins. Publisher: Los Alamos National Laboratory, Theoretical Biology and Biophysics, Los Alamos, N.M. LA-UR 02-4663, at http://hiv-web.lan-1.gov/content/immunology/maps/maps.html.

In one aspect, HIV antigenic peptides matched to particular clades provide the vaccine antigen. The sequences of different clade strains are known in the art and include clade A (Accession No: HIV-1 92UG037WHO.0108HED), B (Accession No: pNL4-3), C (Accession No: HIV-1 92BR025WHO.109HED), D (Accession No: HIV-1 92UG024.2), E (Accession No: HIV-1 93TH976.17), F (Accession No: HIV-1 93BR020.17), and G (Accession No: HIV-1 92RU131.9). For example, the following peptides can be used: from p17—SLFNTVATL (clade A), SLYNTVATL (clade B); from pol A—ILKDPVHG (clade A); ILKEPVHGV (clade B); from p24—DRFFKTLRA (clade A), DLNNMLNI (clade A), PPIPVGDIY (clade A), DLNT-MLNTV (clade B), DRFYKTLRA (clade B), PPIPVGEIY (clade B); from nef—YPLTGWCY (clade B), YPLTFGWCF (clade D). These are epitopes particularly prevalent in African clades. See, e.g., Rowland-Jones, et al. *J Clin. Invest.* 102(9): 1758-65, 1998.

Corresponding SIV sequences are also encompassed within the scope of the present invention.

As discussed above, a vaccine composition according to the invention may provide a plurality of different types of vaccine antigens. For example, for an HIV vaccine, the composition may provide a source of vaccine antigens comprising at least two of any of the HIV antigens described above. Antigens may be from different HIV polypeptides, different strains, different clades, or different regions of the same HIV polypeptide. In one aspect, a panel of peptides representing a mutable region of an HIV polypeptide is provided. The peptides may represent known variants of the region and/or may comprise randomly generated variants.

In another aspect, a vaccine composition according to the invention may provide at least one HIV antigen source and an antigen that enhances a protective immune response against the HIV virus. For example, a universal T cell epitope-containing peptide from hepatitis B surface antigen (amino acids 19-33) is reported to enhance the production of antibodies specific for HIV gp120. See, e.g., Greenstein, et al., *J Immunol.* 148(12): 3970-7, 1992. In yet another aspect, at least one HIV antigen source is provided with an antigen source of an infectious microorganism associated with HIV infection, such as *Pneumocystis cariini* or *Bartonella henselea*.

One preferred multivalent combinations comprises gag, pol and env. Another preferred multivalent combination comprises a gag, pol and reverse transcriptase (RT). Yet another multivalent combination comprises gag, tat and nef.

In another aspect of the invention, the antigen source comprises a bacterial antigen. Bacterial sources of antigens include, but are not limited to, *Bacillus tuberculoses, Bacillus anthracis*, the spirochete *Borrelia burgdoreri* that causes the Lyme disease in animals, and *Bartonella henselea*, the causative agent of cat scratch fever (see, e.g., Renesto, et al., *Res Microbiol.* 151(10): 831-6, 2000; Regnery, et al., *Clin. Infect. Dis.* 21:94-98, 1995).

Parasites also serve as sources of antigens and include, but are not limited to: *Cryptosporidium; Eimeria; Histomonas; Leucocytozoon; Toxoplasmza; Trichoinonas; Leishmania; Trypanosoma; Giardia* (e.g., GenBank Accession No. M33641); *Plasmodium* (e.g., GenBank Accession No. X53832); hookworm; onchocerciasis (e.g., GenBank Accession No. M27807); schistosomiasis (e.g., GenBank Accession No. L08198); trypanosomiasis; amoebiasis, filariasis (e.g., GenBank Accession No. J03266), borreliosis; *Babesia*, and *Theileria*. Antigenic polypeptides of such organisms include coat proteins, proteins of the pathogenic parasites, and the like.

It is contemplated that suitable microorganisms and parasitic antigens will be derived from known causative agents responsible for diseases including, but not limited to, diphtheria, pertussis (e.g., GenBank Accession No. M35274), tetanus (e.g., GenBank Accession-No. M64353), tuberculosis, bacterial and fungal pneumonias (e.g., *Haemophilus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), hepatitis B antigen such as HBeAg, HBcAg and HBsAg (e.g., S, pre-S 1, or pre-S2), ORF 5, ORF 6 (see, e.g., see Blum, et al., *TIG* 5(5): 154-158, 1989); the HBV pol antigen, or a hepatitis C antigen such as the core antigen C, E1, E2/NS1, NS2, NS3, NS4 and NS5

Cancer-specific antigens are also encompassed within the scope of the instant invention. These include, but are not limited to: a polypeptide comprising an epitope derived from Her-2/neu; gp100; MAGE proteins (MAGE 1, e.g., GenBank Accession No. M77481; MAGE 2, e.g., GenBank Accession No. U03735; MAGE 3, MAGE 4); TAG-72; CEA; MART; tyrosinase-related-protein 1 and 2 (TRP-1, TRP-2) (see, e.g., Boon et al., *Immunol Today* 16: 334-336, 1998); CD20; Mucin 1 (e.g., GenBank Accession No. J03651) and Mucin 2; p53 (see e.g., Harris, et al., *Mol. Cell. Biol.*, 6: 4650-4656, 1986) and is deposited with GenBank under Accession No. M14694); mutant p53 (e.g., GenBank Accession No. X54156 and AA494311); p21/ras, p210/bcr-abl fusion polypeptides; c-myc; p97 melanoma antigen (e.g., GenBank Accession No. M12154); blood antigens T, Tn and sialyl-Tn; tuncated form of EGF; Lewis-Y antigen; squamous cell carcinoma antigens (see, e.g., sequences described in U.S. Pat. No. 5,763,164); prostate specific antigen (PSA; Osterling, *J. Urol.* 145: 907-923, 1991; GenBank Accession No. X14810); epithelial membrane antigen (Pinkus et al., *Am. J. Clin. Pathol.* 85: 269-277, 1986); CYFRA 21-1 (Lai et al., 199 *Jpn. J. Clin. Oncol.* 29: 421-421, 1999) and Ep-CAM (Chaubal et al., Anticancer Res. 19: 2237-2242, 1999). Epstein-Barr virus gene products also encode antigenic polypeptides which are expressed in Hodgkin's lymphomas as well as Burkits and other lymphomas. Products of the HTLV-1 genome have been found in adult T cell leukemia cells, while human papillomavirus (HPV) E6 and E7 gene products are found in cervical carcinoma cells. In addition, Human herpesvirus 8 (HHV8) genomic products have been found in Kaposi sarcomas.

Examples of transplant antigens include the CD3 receptor on T cells. Treatment with an antibody to CD3 receptor has been shown to rapidly clear circulating T cells and reverse most rejection episodes.

Examples of autoimmune antigens include IAS chain. Vaccination of mice with an 18 amino acid peptide from IAS chain has been demonstrated to provide protection and treatment to mice with experimental autoimmune encephalomyelitis. Autoimmune polypeptides found in patients with system lupus are also encompassed within the scope of the invention (e.g., GenBank Accession No. D28394; Bruggen et al., *Ann. Med Interne* 147: 485-489, 1996). Additional antigens include β-amyloid antigens.

Antigenic peptides can also include allergens such as the Der p I allergen (Hoyne, et al., *Immunol.* 83: 190-195, 1994); bee venom phospholipase A2 (PLA) (Akdis, et al., *J. Clin. Invest.* 98:1676-1683, 1996); birch pollen allergen Bet v 1 (Bauer, et al., *Clin. Exp. Immunol.* 107: 536-541, 1997), and the multi-epitopic recombinant grass allergen rKBG8.3 (Cao, et al., *Immunol.* 90: 46-51, 1997).

New antigens also can be identified using methods well known in the art. Any conventional method, e.g., subtractive library, comparative Northern and/or Western blot analysis of normal and tumor cells, Serial Analysis of Gene Expression (U.S. Pat. No. 5,695,937) and SPHERE (described in PCT WO 97/3 5 03 5), can be used to identify putative antigens for use.

Differential screening of nucleic acid sequences expressed by the two cell lines can be used to select sequences encoding antigens specific to cancer cells, and even specific stages of cancer cells. When the non-target cell is a normal cell, differential screening eliminates or reduces the nucleic acid sequences common to normal cells, thereby avoiding an immune response directed at antigens present on normal cells. When the non-target cell is a normal cell, differential screening eliminates or reduces sequences common to normal cells, thereby avoiding an immune response directed at antigens present on normal cells.

For example, expression cloning as described in Kawakami et al., 1994, *Proc. Natl. Acad. Sci.* 91: 3515-19, also can be used to identify a novel tumor-associated antigen. Briefly, in this method, a library of cDNAs corresponding to mRNAs derived from tumor cells is cloned into an expression vector and introduced into target cells which are subsequently incubated with cytotoxic T cells. Pools of cDNAs that are able to stimulate T Cell responses are identified and through a process of sequential dilution and re-testing of less complex pools of cDNAs, unique cDNA sequences that are able to stimulate the T cells and thus encode a tumor antigen are identified. The tumor-specificity of the corresponding mRNAs can be confirmed by comparative Northern and/or Western blot analysis of normal and tumor cells.

SAGE analysis can be employed to identify the antigens recognized by expanded immune effector cells such as CTLs, by identifying nucleotide sequences expressed in the antigen-expressing cells. SAGE analysis begins with providing complementary deoxyribonucleic acid (cDNA) from an antigen-expressing population and cells not expressing the antigen. Both cDNAs can be linked to primer sites. Sequence tags are then created, for example, using appropriate primers to amplify the DNA. By measuring the differences in these tag sets between the two cell types, sequences which are aberrantly expressed in the antigen-expressing cell population can be identified.

Another method to identify optimal epitopes and new antigenic peptides is a technique known as Solid PHase Epitope REcovery ("SPHERE"). This method is described in detail in PCT WO 97/35035. Although used to screen for MHC class I-restricted CTL epitopes, the method can be modified to screen for class II epitopes by screening for the stimulation of antigen-specific MHC class II specific T cell lines, for example, rather than CTL. In SPHERE, peptide libraries are synthesized on beads where each bead contains a unique peptide that can be released in a controlled manner. Eluted peptides can be pooled to yield wells with any desired complexity. After cleaving a percentage of the peptides from the beads, these are assayed for their ability to stimulate a Class I or Class II response, as described above. Positive individual beads are then be decoded, identifying the reactive-amino acid sequence. Analysis of all positives will give a partial profile of conservatively substituted epitopes which stimulate the T cell response being tested. The peptide can be resynthesized and retested to verify the response. Also, a second library (of minimal complexity) can be synthesized with representations of all conservative substitutions in order to enumerate the complete spectrum of derivatives tolerated by a particular response. By screening multiple T cell lines simultaneously, the search for crossreacting epitopes can be facilitated.

Suitable antigen portions of polypeptides portions may be readily identified by synthesis of relevant epitopes, and analysis using methods routine in the art (see, e.g., Manca et al. *Eur. J. Immunol.* 25:1217-1223, 1995; Sarobe, et al., *J. Acquir. Immune Defic. Syndr.* 7: 635-40, 1994; Shirai, et al., J. Immunol. 152: 549-56, 1994; Manca, et al., *Int. Inmunol.* 5: 1109-1117, 1993; Ahlers, et al., *J. Immunol.* 150: 5647-65, 1993; Kundu and Merigan, *AIDS* 6: 643-9, 1992; Lasarte, et al. *Cell Immunol.* 141: 211-8, 1992; and Hosmalin et al., *J. Immunol.* 146: 1667-73, 1991).

Isolated peptides can be synthesized using an appropriate solid state synthetic procedure (Steward and Young, *Solid Phase Peptide Synthesis*, Freemantle, San Francisco, Calif. 1968). A preferred method is the Merrifield process (Merrifield, *Recent Progress in Hormone Res.* 23: 451, 1967). Once an isolated peptide is obtained, it may be purified by standard methods including chromatography (e.g., ion exchange, affinity, and sizing column chromatography), centrifugation, differential solubility, or by any other standard technique for protein purification. For immunoaffinity chromatography, an epitope may be isolated by binding it to an affinity column comprising antibodies that were raised against that peptide, or a related peptide, and were affixed to a stationary support. Alternatively, affinity tags such as hexa-His (Invitrogen), Maltose binding domain (New England Biolabs), influenza coat sequence (Kolodziej, et al., *Methods Enzymol.* 194: 508-509, 1991), and glutathione-S-transferase can be attached to the peptides to allow easy purification by passage over an appropriate affinity column.

Isolated peptides also can be physically characterized using such techniques as proteolysis, nuclear magnetic resonance, and x-ray crystallography. Antigen mimitopes may be selected for that mimic conformationally dependent antigenic epitopes as determined by their ability to bind to conformationally dependent, neutralizing antibodies.

Selection of the most appropriate portion of the desired antigen protein for use as the antigenic domain can be done by functional screening. The particular screening procedure depends upon the type of antigen and the assays for its antigenic activity. Antigenicity may be measured by stimulation of antigen-specific MHC/HLA class I or MHC/HLA class II specific T cell line or clone. Alternatively, antigenicity may be determined by measurement of the ability to generate antibodies or T cells specific for the antigen in vivo.

In one aspect, epitopes are identified which are recognized by specific HLA haplotypes. For example, peripheral blood monocytes (PBMCs) obtained from HIV-infected donors and expanded cultures are obtained by restimulation with autologous PHA-stimulated lymphoblasts for about a week. CTLs are cultured in a suitable culture medium, e.g., such as RPMI 1640 (Gibco Life Technologies, Glasgow, Scotland); 10% FCS (Gibco Life Technologies), antibiotics, and 10% Lymphocult T (Biotest, Solihull, England) (IL-2) for another week.

Standard $^{51}$-Chromium release assays are performed using HLA-matched or mismatched target B-lymphoblastoid cell lines labeled with 51-chromium (Amersham, Buckinghamshire, England) and pulsed with a pool of epitope peptides predicted to bind to the HLA molecule or a control peptide (e.g., such as an influenza antigen) at about 50 μM in multiple different wells of a microtiter plate. Individual peptides from a pool which reacts with the HLA molecule to stimulate a CTL response are then tested to identify the specific reactive peptide epitope. Chromium is counted in a scintillation counter (e.g., such as available at Wallac, Gaithersburg, Md.) and percent lysis calculated from the formula 100×(E-M/T-M), where E is the experimental release of chromium, M is release in the presence of medium without detergent (i.e., release which occurs because of a CTL response), and T is release in the presence of 5% Triton X-100 detergent. Results are regarded as positive if recognition of the HIV peptide is >10% above that of a control peptide in at least two separate assays.

Immunogenic portions may also be selected or validated in animal models. For example, the HLA A2. 1/Kb transgenic mouse has been shown to be useful as a model for human T-cell recognition of viral antigens. In both the influenza and hepatitis B viral systems, the murine T-cell receptor repertoire recognizes the same antigenic determinants recognized by human T-cells. In both systems, the CTL response generated in the HLA A2.1/Kb transgenic mouse is directed toward virtually the same epitope as those recognized by human CTLs of the HLA A2.1 haplotype (Vitiello et al., *J. Exp. Med.* 173: 1007-1015, 1991; Vitiello et al., *Abstract of Molecular Biology of Hepatitis B Virus Symposia,* 1992). In CTL induction in mice may be utilized to predict cellular immunogenicity in humans (see, Warner et al., *AIDS Res. and Human Retroviruses* 7: 645-655, 1991).

Alternatively, or additionally, immunogenic regions of a polypeptide may be identified using computer programs for identifying conserved regions amongst different pathogenic strains of an organism or polypeptides associated with a pathology (e.g., such as an autoimmune disease) and/or to identify regions that bind to particular MHC haplotypes (see, e.g., Falk, et al., *Nature* 351: 290, 1991). A number of software programs are known in the art. For example, Peptgen generates maps of overlapping peptides. Motifscan scans polypeptide sequences for possible epitopes based on HLA binding motifs, while ELF (Epitope Location Finder Tool) may be used to identify potential CTL epitopes. From this analysis, peptides can be validated in appropriate in vitro or in vivo assays.

Having isolated and identified the peptide sequence of a desired epitope, nucleic acids comprising sequences encoding these epitopes can be sequenced readily.

The immunogenic portion(s) which are incorporated into an expression construct (i.e., a nucleic acid molecule comprising an expression control sequence operably linked to the immunogenic portion or antigen-encoding sequence) may be of varying length, although it is generally preferred that nucleic acid encode a portion at least about 8-30 amino acids long, more preferably, 8-24 amino acids long. As discussed above, in some cases it is desirable to provide repeating units of antigens optionally separated by linker sequences or linked to helper sequences to facilitate recognition by an appropriate MHC/HLA molecule.

Antigen-Encoding Vector Constructs

Antigenic material can be administered to a host organism simultaneously along with the IL-15-encoding viral vector or shortly before or after administration of the vector.

When isolated polypeptide vaccines are injected into a host, the antigen is presented from the outside of the host cell and often does not generate strong, long-lasting immune response, since the polypeptide is not processed appropriately and is susceptible to rapid clearance. Therefore, preferably, antigenic material is provided by administering nucleic acids encoding the antigen.

Expression constructs comprising a nucleic acid sequence encoding at least one antigen operably linked to a promoter can be administered as linear fragments or circular molecules along with the recombinant IL-15 vector. The constructs may further comprise at least one origin of replication for replicating in at least one type of host cell for amplification of the vector (e.g., such as *E. coli*). Antigen encoding expression constructs can be administered to the host organism as naked DNA or in a delivery vehicle associated with one or more molecules for facilitating entry of the expression construct into the cell. Suitable molecules include, but are not limited to: liposomes; polypeptides; polysaccharides; lipopolysaccharides; cationic molecules; viral particles, and the like.

The antigen encoding expression unit may also be provided in the form of a viral vector and the vector may be the same or different as the recombinant IL-15-expressing vector. In one aspect, the vector is a poxvirus vector, such as a vaccinia virus vector. In another aspect, the antigen-encoding expression unit is part of the same viral vector encoding IL-15. In one aspect, expression of both the antigen and IL-15 is under the control of individual poxvirus promoters.

The temporal course of expression of IL-15 and antigen may be the same or different. For example, both IL-15- and antigen-encoding sequences may be under the control of an early, intermediate, or late promoter. However, in another aspect, the sequences are under the control of promoters such that IL-15 and antigen show different temporal expression patterns, e.g., IL-15 is expressed first or antigen is expressed first. Preferably, the antigen encoding sequence is under the control of a strong promoter, such as an early/late hybrid promoter p7.5 to ensure its expression throughout the replicative cycle of the virus. In still another aspect, the nucleic acid sequence encoding IL-15 and the nucleic acid encoding the vaccine antigen are expressed coordinately on a single polycistronic mRNA (i.e., by including one or more IRES sequences in the vector). See, for example, as described in EP 0 803 573.

Enhancing and/or Inducing Immune Responses

Vertebrates exploit two basic strategies to mount immune responses against antigens. Humoral immunity involves the direct recognition of antigens by antibodies. Cellular immunity relies on special cells which recognize and kill other cells which are producing foreign antigens. Humoral immunity is mainly directed at antigens which are exogenous (e.g., extracellular) whereas the cellular system generally provides a response to intracellular antigens.

The humoral system protects a vaccinated individual from subsequent challenge from a pathogen and can prevent the spread of an intracellular infection if the pathogen goes through an extracellular phase during its life cycle; however, it can do relatively little to eliminate intracellular pathogens. Cytotoxic immunity complements the humoral system by eliminating the infected cells.

In a natural process of viral infection, virus-infected cells display viral antigens on their surface in the context of the MHC-I or HLA class I receptor, while viral particles are digested by professional antigen-presenting cells and display antigens in association with MEC-II or HLA class II receptors. Both humoral and cellular responses are necessary to prevent new infection. While cytotoxic T cells (recognizing antigens presented in the context of MHC I/HLA-I molecules) and antibodies are required to remove extracellular pathogens, memory cells (i.e., CD4+ cells recognizing antigens presented in the context of MHC II) are required to prevent re-infection. However, cytotoxic T cells (CD8$^+$ T cells) can also provide a source of memory T cells, providing long lasting CTL responses after an initial exposure to antigen. Thus, effective vaccination should activate all of these types of immune responses The vaccine compositions according to the invention are used to induce and/or enhance one or more immune responses. Such immune responses generally involve one or more of: production of antibodies specific for a selected antigen; and production of antigen specific T cells (e.g., helper cells, suppressor cells, and/or cytotoxic cells). Preferably, the immune response comprises a memory response that results in the production of memory CD8$^+$ T cells and vaccine antigen-specific antibodies.

Preferably, the compositions according to the invention induce sustained polyclonal crossreactive CTL responses. In one aspect, individuals vaccinated with compositions according to the invention have a circulating frequency of CTL to vaccine antigens of between about 1:2000 and 1:50,000 as determined by Elispot analysis up to at least about 4 months, at least about 8 months, at least about 10 months, at least about 12 months, at least about 14 months, at least about 16 months, at least about 18 months, at least about 20 months, at least about 22 months, and at least about 24 months, Methods for performing Elispot analysis are known in the art and described in Vogel, *J. Clin. Invest.* 102: 1758-1765, for example.

The assay detects peptide-specific CTL-mediated IFN-γ release from peripheral blood mononuclear cells (PBMCs). In one aspect, to perform the assay, 96-well nitrocellulose plates are coated with an antibody to IFN-γ (e.g., available from Mabtech, Stockholm, Sweden) and PBMC are placed in wells at varying concentrations (e.g., $2 \times 10^5$, $10^5$ and $5 \times 10^4$), preferably in duplicate.

Suitable autologous target cells are pulsed with either no peptide or one of a panel of peptides selected according to the class I HLA-type of a particular donor, at a final concentration of 10 μM, and the plate is incubated at 37° C., 5% CO$_2$ for about 16 hours allowing IFN-γ released by PBMCs to be detected by monitoring antibody binding. Binding can be visualized using detector and conjugate antibodies followed by chromogen to detect a color change as is well known in the art. The assays are regarded as positive if there is greater than about 10% specific lysis of peptide-pulsed target cells at two different effector/target (E/T) ratios in at least two separate experiments. Control assays are carried out under identical conditions by using cells from uninfected patients with the same class I alleles.

In one aspect, compositions according to the invention are screened to identify those which elicit the production of neutralizing antibodies. The presence of neutralizing antibodies can be detected by premixing a virus sample and antibody sample (e.g., obtained from sera of a vaccinated patient), inoculating PBMCs or a cell line, culturing for a suitable time period (e.g., up to about two weeks) and measuring viral replication (e.g., via a p24 or reverse transcriptase assay) or by detecting a lack of cytopathic effect in the cells (e.g., by trypan blue or by monitoring syncytia formation). A decrease in infectivity or cell death indicates that the antibody sample is capable of neutralizing the virus. A decrease in infectivity is reflected by decreased levels of p24 or reverse transcriptase with respect to controls which have not been exposed to antibody while a decrease in cell death is indicated by significantly fewer dead cells and/or syncytia.

PCR assays may also be used to detect the presence of neutralizing antibodies. In one aspect, antibody and virus samples are mixed with cells. After a suitable incubation period (e.g., 2-5 hours), cells are collected and PCR is performed to detect viral sequences (such as the LTR or gag sequences). A decrease in amplified products compared to controls lacking antibody is an indicia of neutralization (i.e., fewer infection events). Antibody and virus samples are mixed and applied to cells. After several hours, cells are collected, DNA isolated and PCR performed to detect LTR or gag region DNA. The PCR products are quantitated and compared to controls lacking antibody. Neutralization is defined as a decrease in the PCR signal, which correlates with fewer infection events.

In still another aspect, a MAGI assay is performed to measure virus infectivity. In this assay, HeLa cells stably transfected with CD4 and a γ-galactosidase gene modified to localize to the nucleus operably linked to a truncated HIV-1 LIR which is activated by Tat. Thus, expression of γ-galactosidase is dependent on the level of Tat which in turn is dependent on the presence of virus. The Hela cells will stain blue and the number of blue cells in a population will be proportional to the number of infectious particles in an inoculum.

Efficacy of a vaccine composition also can be evaluated by monitoring the level of the selected antigen and/or the presence of antibodies in sera which specifically cross-react with the antigen. For example, the efficacy of HIV vaccines can be monitored by measuring viral titer at selected time intervals such as by performing an immunoassay using an antibody specific for the HIV. Highly sensitive nucleic acid-based tests may also be employed as described in EP 617, 132, WO 94/20640, WO 92/02526 and U.S. Pat. Nos. 5,451,503 and 4,775,619 for example. Viral load can be monitored by measuring an amount of HIV RNA in plasma, cells or tissue from a patient. Subsequent monitoring of the patient can include periodic diagnostic tests following administration of the vaccination therapy.

Vaccines may be tested initially in a non-human mammal (e.g., a mouse or primate) as described further below in Examples 1-3. For example, assays of the immune responses of inoculated mice can be used to demonstrate greater antibody production, T cell proliferation, and cytotoxic T cell responses to the vaccine compositions according to the invention. Vaccines can be evaluated in Rhesus monkeys to determine whether a vaccine formulation that is highly effective in mice will also elicit an appropriate monkey immune response.

Dosage and Routes Of Administration

The invention further provides pharmaceutical compositions comprising recombinant IL-15 expressing poxvirus vectors and at least one antigen source (i.e., the vaccine antigen). Preferably, the antigen source is an expression construct comprising a nucleic acid sequence encoding at least one antigen operably linked to an expression control sequence. Also, preferably, the composition comprises a pharmaceutically acceptable diluent, carrier, or excipient carrier. Additionally the vaccine may also contain an aqueous medium or a water-containing suspension, to increase the activity and/or the shelf life of the vaccine. The medium/suspension can include salt, glucose, pH buffers, stabilizers, emulsifiers, and preservatives.

In addition to IL-15, other adjuvants may be included, e.g., including, but not limited to: muramyl dipeptide; aluminum hydroxide; saponin; polyanions; anamphipatic substances; bacillus Calmette-Guerin (BCG); endotoxin lipopolysaccharides; keyhole limpet hemocyanin (GKLH); and cytoxan. However, it is a discovery of the instant invention that IL-15 can potentiate a long-term immune response without necessitating the use of other adjuvants.

The invention also encompasses a kit including a recombinant poxvirus encoding IL-15 and a nucleic acid encoding an antigen. The recombinant poxvirus can be provided in lyophilized form for reconstituting, for instance, in an isotonic aqueous, saline buffer. The kit can include a separate container containing a suitable carrier, diluent or excipient. The kit can also include an additional therapeutic agents, such as anti-cancer agents; agents for ameliorating symptoms of a viral infection (e.g., such as a protease inhibitor, Cimetidine (Smith/Kline, Pa.), low-dose cyclophospharide (Johnson/Mead, N.J.); and the like); and genes encoding proteins providing immune helper functions (such as B-7); and the like. In one aspect, the kit alternatively, or additionally, includes an antigen presenting cell. Additionally, the kit can include instructions for mixing or combining ingredients and/or administering the kit components.

In one aspect, the invention provides a method of administering a therapeutically effective vaccine compositions according to the invention. The desired therapeutic effect comprises one or more of: reducing or eliminating viral load, increasing numbers of $CD4^+$ and/or $CD8^+$ T cells or antibodies which recognize the vaccine antigen; increasing overall levels of $CD4^+$ T cells; increasing levels of neutralizing antibodies which recognize the antigen; decreasing the number of or severity of symptoms of a disease; decreasing the expression of a cancer specific marker; decreasing size or rate of growth of a tumor; preventing metastasis of a tumor; preventing infection by a pathogenic organism; and the like. The therapeutic effect may be monitored by evaluating biological markers and/or abnormal physiological responses. Generally, an effective dose of a composition according to the invention comprises a viral titer that can modulate an immune response against the vaccine antigen such that memory T cells are generated which are specific for the vaccine antigen.

Both the dose and the administration means can be determined based on the condition of the patient (e.g., age, weight, general health), risk for developing a disease, or the state of progression of a disease. A preferred route of administration is by intradermal scarification when the delivery vaccine vector is a poxvirus.

In one aspect, an effective amount of recombinant virus ranges from about 10 µl to about 25 µl of saline solution containing concentrations, preferably, of from about $1\times10^{10}$ to $1\times10^{11}$ plaque forming units (pfa) virus/ml.

In a preferred aspect of the invention, a priming immunization is performed, followed, optionally, by a booster immunization at about 3-4 weeks after the priming immunization. However, subsequent immunizations need not be provided until at least about 4 months, about 6 months, about 8 months, about 12 months, about 10 months, about 16 months, about 18 months, or about 24 months after the priming boost. In one aspect, the vaccine is a prophylactic vaccine, administered to a patient who has not been exposed to the vaccine antigen, e.g., such as to an individual who is HIV negative. In another aspect, the vaccine is administered therapeutically, to a person who is seropositive for the vaccine antigen (although not necessarily displaying symptoms) (i.e., such as to an HIV positive individual). In a further aspect, the vaccine is administered to an immunodeficient individual. In this aspect, the vaccine preferably is derived from a replication defective virus such as MVA or AVIPOX.

EXAMPLES

The invention will now be further illustrated with reference to the following examples. It will be appreciated that what follows is by way of example only and that modifications to detail may be made while still falling within the scope of the invention.

Example 1

Dual Recombinant HIV gp160/IL-15 Increases the Magnitude and Duration of Cellular Immune Responses To demonstrate that co-delivery of immunostimulatory cytokines with HIV antigens would result in a more robust immune response, two recombinant vaccinia viruses that express HIV-1 gp160 in tandem with either human IL-2 or human IL-15 were generated. The coding region of the human IL-15 gene was cloned into transfer vector pSC11 for recombination with the WR vaccinia strain, commercially available from the American Type Culture Collection (ATCC No. VR-119).

To create recombinant vaccinia expressing human IL-15, the coding region of IL-15 including 3 nucleotides upstream of the start codon, ATG, and the entire coding region of IL-15 including the TGA terminator codon and 4 nucleotides downstream of the terminator codon, was used. The plasmid from which IL-15 sequences were obtained is described in Burton, et al., *Proc. Natl. Acad. Sci. USA* 91: 4935-4939.

To create recombinant vaccinia expressing human IL-2, the coding region of the human IL-2 gene was derived from the pTCGF-11 plasmid obtained from ATCC catalog number 39673 as a 0.8 kb Pst-1 fragment including in addition to the coding sequence, 17 nucleotides upstream of the start codon, ATG, and the entire coding region of IL-2, including the terminator codon and 250 nucleotides downstream of the terminator codon.

The pSC11 transfer vector (see, e.g., Toth, et al., *Vet. Microbiol.* 45(2-3): 171-83, 1995) used for integration of IL-2 or IL-15 into the thymidine kinase ("tk") gene locus of the vaccinia genome. In recombinants carrying only the cytokine (e.g., either IL-15 vaccinia or IL-2 vaccinia), the respective cytokine was integrated into the tk locus with insertional inactivation of the viral tk gene.

The original pVOTE1 vector has been described in Ward, et al., *Proc. Natl. Acad. Sci. USA* 92: 6773. In modifying the pVOTE1, the DNA sequence between the Apa-I site and Sma-I site was removed and replaced by a sequence having an early/late vaccinal promoter: 5'-CACCCATAAATAATAA-ATACAATAATTAATTTCTCGTAAAAGTAGAAAATAT-ATTCTAATTTATTGCACGGTAAGGAAGTAGAATCAT-AAAGAACAGTGACGGATCCC-3' (SEQ ID NO: 1). This modified plasmid was then used for integration of IL-2 or IL-15 into the hemagglutinin gene locus of vaccinia genome. In the dual recombinants which express both HIV gp160 and either IL-2 or IL-15, a HIV vaccinia viral vector comprising gp160 was intergrated into the tk locus as described in Earl, et al., *J. Virol.* 65: 31-41, 1991) used to intergrate either human IL-2 or IL-15-encoding sequences using the modified pVOTE transfer vector comprising either IL-2 or IL-15 inserted into the hemagglutinin locus.

The immune responses of mice virus inoculated with virus recombinants over a period of 14 months, were strikingly different in terms of CTL activity, both in magnitude and duration. Inbred Balb/c female mice were immunized subcutaneously (at the base of the tail) with $6\times10^6$ pfu in 100 µl volume. After 3-4 weeks, animals were boosted with the same dose of the respective virus as the primary immunization.

Figure 2:
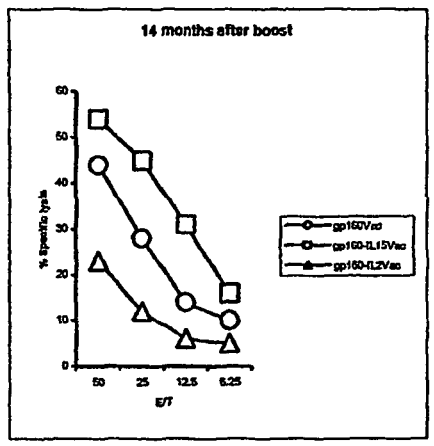
FIG. 2 is a graph showing percent specific lysis of HIV-1 gp120 peptide-pulsed cells by $CD8^+$ T cells obtained from mice 14 months after receiving recombinant vaccinia viruses according to the invention expressing both IL-15 and the gp160 antigen, both IL-2 and gp160, or gp160 alone. "E/T" refers to effector/target cell ratio.

The data shown in FIGS. 1 and 2 depict $CD8^+$ cells displaying cytolytic activity towards HIV-1 gp120 peptide-pulsed target cells. Splenic CD8+ T cells from each group of animals were stimulated in vitro with 1.0 nM of immunodominant HIV gp120 V3 loop peptide P18-I10 for 7 days. These in vitro stimulated cells were used as effector cells to lyse cognate peptide-pulsed P815 fibroblasts (H-2D$^d$ haplotype) target cells in a 5 hour $^{51}$Cr release assay. While the early response was superior in the IL-2 group, in the late phase IL-15 group displayed a more robust response.

As can be seen from the Figures, antigen-specific CTL responses in mice receiving the recombinant IL-15 vector lasted much longer than CTL responses observed in mice receiving recombinant IL-2, e.g., to at least 14 months after the initial injection.

Figure 3:
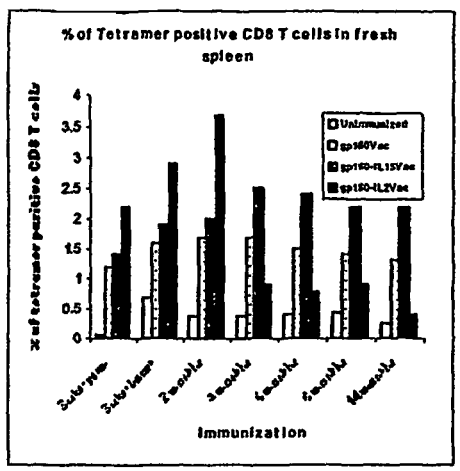
FIG. 3 is a bar graph showing percent of HIV gp120 V3 loop peptide (P18-I10) tetramer positive CD8+ T cells in fresh spleen in unimmunized mice, in mice receiving recombinant vaccinia virus expressing HIV gp160, and in mice receiving vaccinia virus co-expressing gp160 and IL-15 or IL-2 at various time periods after immunization.

The presence of antigen-specific CD8+ was quantitated using labeled H2D$^d$-p18-I10 tetramer using an assay as described in Klenerman, et al., *Nature Reviews/Immunology* 2: 263-272, 2002. As shown in FIG. 3, CD8+ T cells positive for an immunodominant gp120 were present in both groups of mice as determined by tetramer staining. Mice receiving recombinant IL-15 comprised approximately four times as many gp120 specific CD8+ T cells as mice receiving recombinant IL-2.

Figure 4:
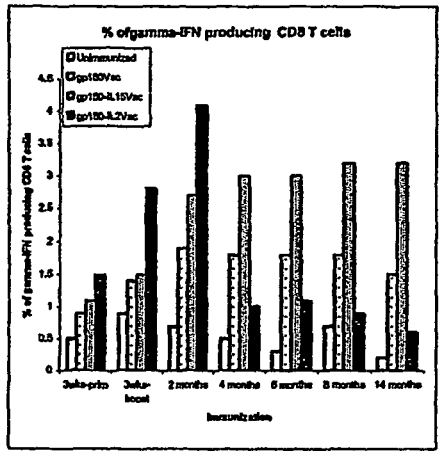
FIG. 4 is a bar graph showing percent of γ-IFN-producing CD8 T cells upon exposure to HIV gp120 V3 loop P18-I10 peptide pulsed cells at various time periods after immunization in unimmunized mice, in mice receiving recombinant vaccinia virus expressing HIV gp160, and in mice receiving vaccinia virus co-expressing gp160 and IL-15 or IL-2.

As shown in FIG. 4, CD8+ T cells that produce γ-interferon upon exposure to an immunodominant HIV-1 gp120 peptide (i.e., memory CD8+ cells) are present at much higher levels (approximately 4-fold) in mice vaccinated with vaccinia expressing gp160 with IL-15 compared to mice vaccinated with vaccinia expressing gp160 with IL-2 at 14 months, indicating long term potentiation of memory CD8+ cells.

Thus, in all tests used, while the group of mice that received the HIV gp160/IL-2 formulation responded vigorously, by generating a gp120-specific CTL activity initially, the duration and the magnitude of this CTL response was relatively short-lived. The level of CTL activity in this group dropped to that of the baseline unvaccinated control group by about 120 days post vaccination. In contrast, the group of mice that received the gp160/IL 15 formulation maintained high levels of gp120-specific CTL activity beyond 14 months post vaccination (compare FIG. 1 vs FIG. 2).

Example 2

Dual Recombinant Antigen/IL-15 Constructs Enhance Humoral Immune Responses

Figure 5:
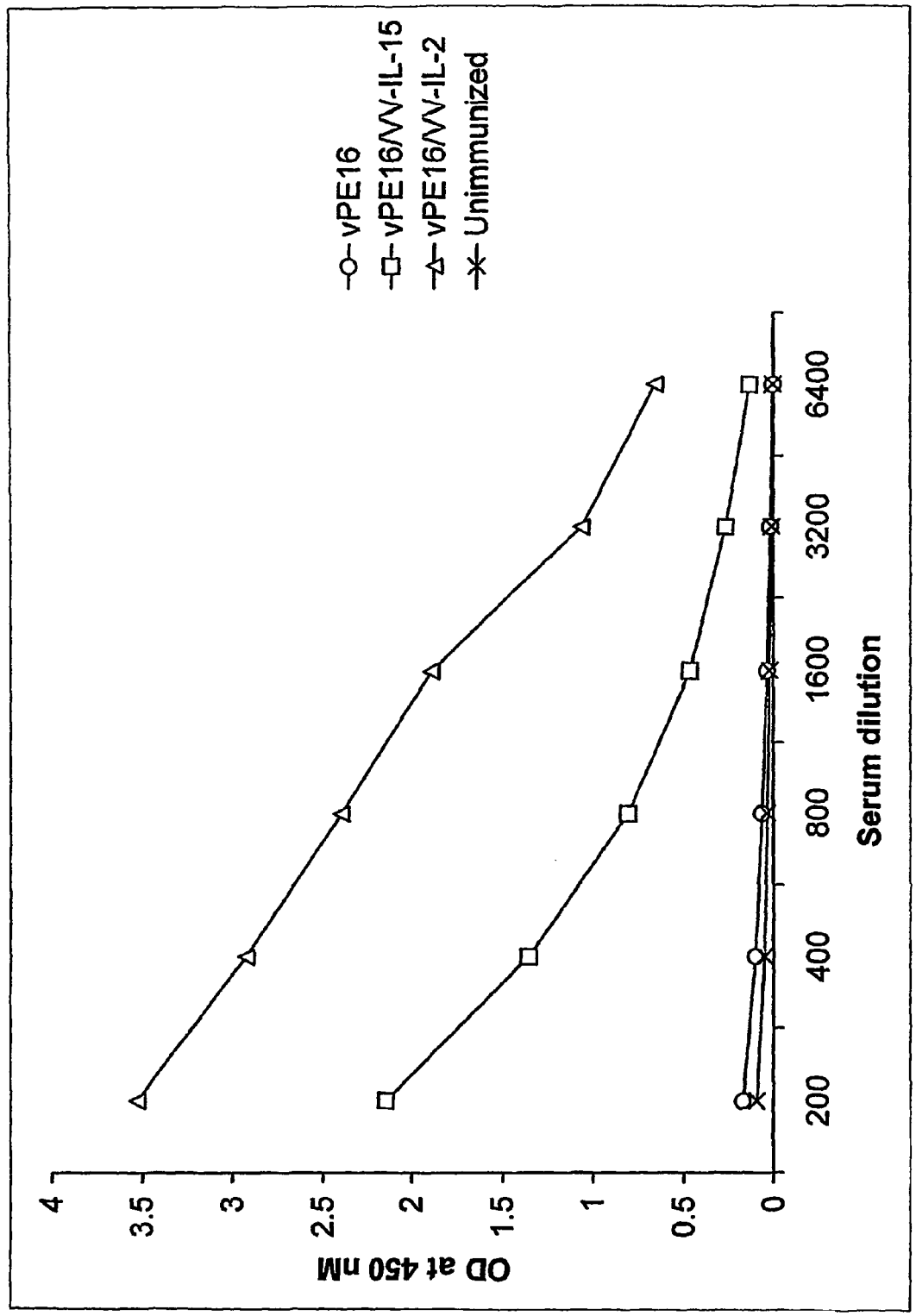
FIG. 5 shows anti-gp120 antibody titer in unimmunized mice, in mice receiving recombinant vaccinia virus expressing HIV gp160, and in mice receiving vaccinia virus co-expressing gp160 and IL-15 or IL-2 at 8 months after immunization.

Levels of antibodies specific for HIV gp120 in the sera of vaccinated animals were evaluated by ELISA, using methods routine in the art. Levels of gp120 specific antibody in mice vaccinated with vaccinia that expressed HIV gp160 alone were undetectable at 8 months after vaccination (i.e., no different from unvaccinated animals). However, mice that were vaccinated with the dual recombinant vaccinia expressing HIV gp160 in tandem with IL-15 displayed high levels of gp120-specific antibodies even at this late time point (see, FIG. 5).

Example 3

Recombinant Her-2/neu Vaccine Vectors

A plasmid comprising a human Her-2/neu encoding sequence as described in Ye, et al., Mol. Cell. Biol. 16: 6178-6189, 1996 was used to obtain the coding region of Her-2/neu which was subsequently cloned into pSC11 and integrated into the tk locus of WR strain of vaccinia to generate a Her-2/neu vaccinia virus vector. The Her-2/neu/IL-15 dual recombinant was generated by integrating IL-15 into the hemagglutinin locus of the recombinant Her-2/neu vaccinia vector using the modified pVOTE vector comprising IL-15.

Recombinants were created in WR strain (ATCC# VR-119), Wyeth Strain (ATCC# VR-1536) and MVA strain (ATCC-VR1508) backbones and animals were vaccinated as described in the above Examples.

Figure 6:
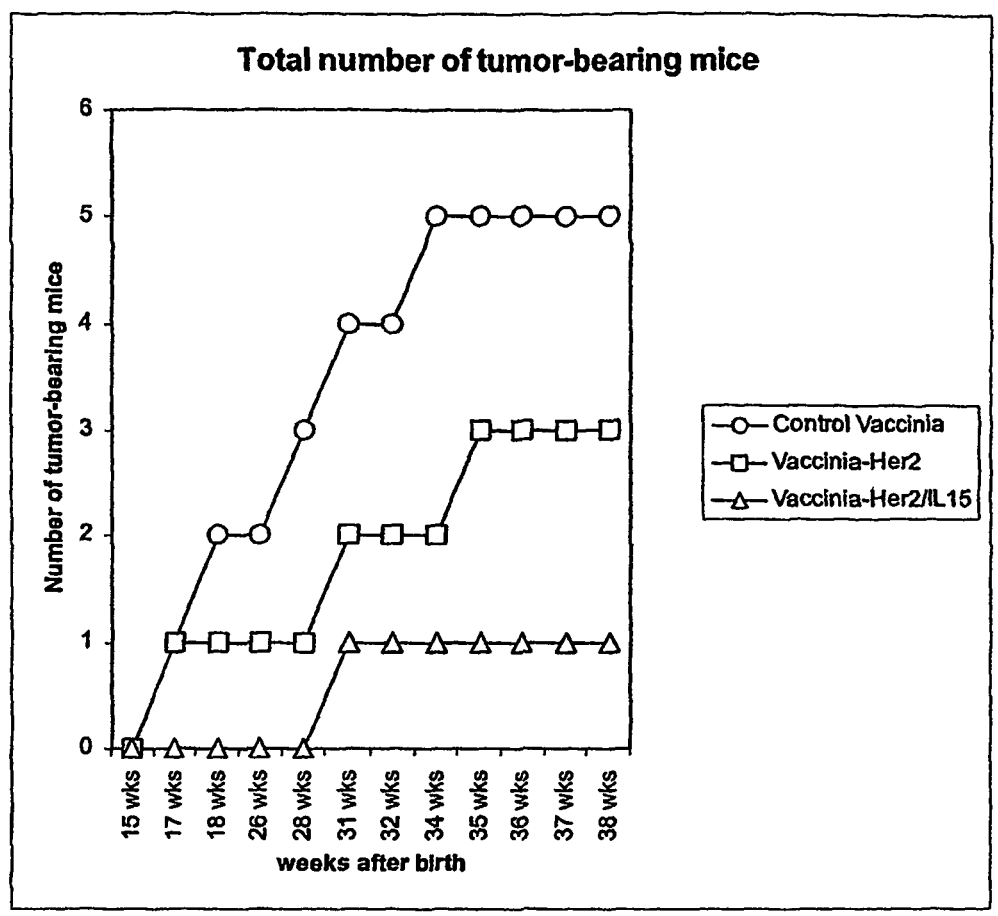
FIG. 6 is a graph showing numbers of tumor-bearing mice at various time intervals after receiving a recombinant vaccinia virus expressing Her-2/neu, both Her-2/neu and IL-15, or a control vaccinia virus.
Figure 7:
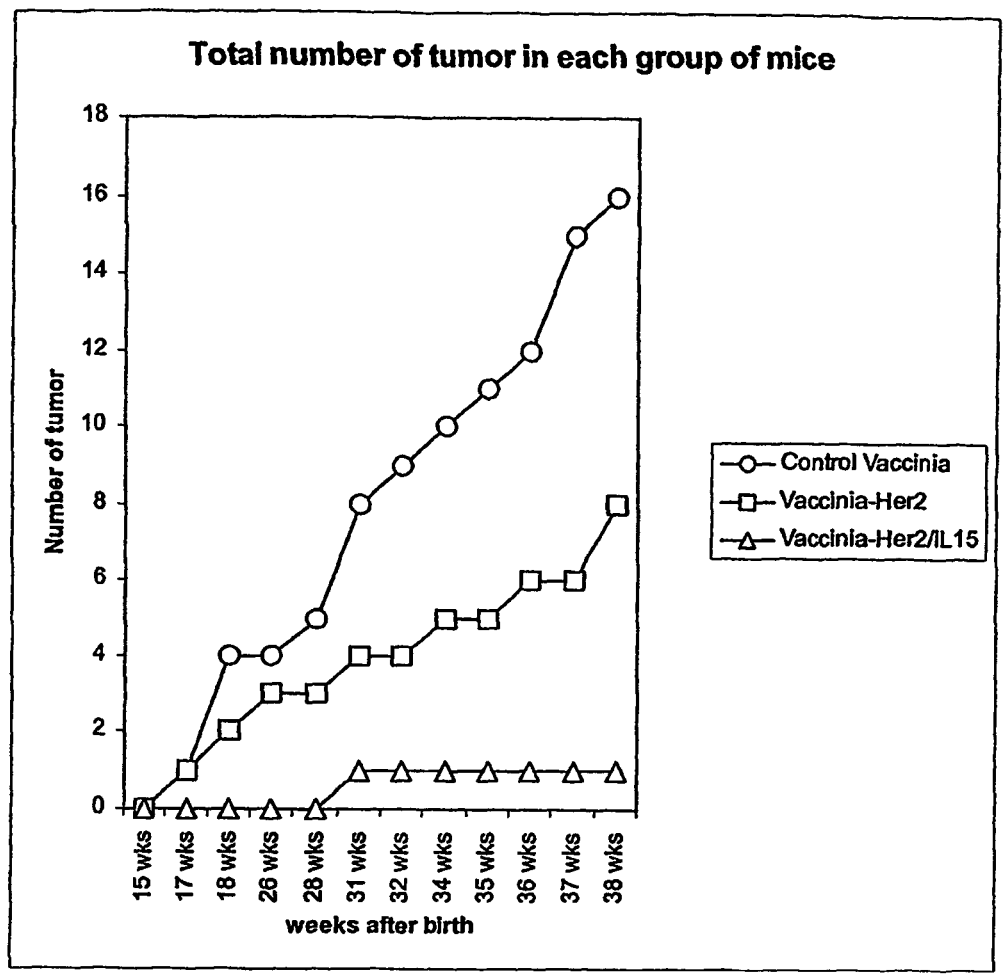
FIG. 7 is a graph showing numbers of tumors in tumor-bearing mice after receiving a recombinant vaccinia virus expressing Her-2/neu, both Her-2/neu and IL-15, or a control vaccinia virus.
Figure 8:
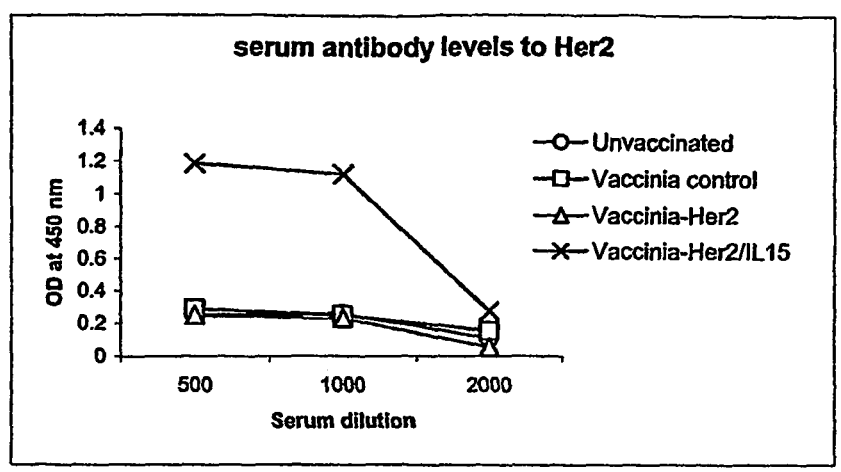
FIG. 8 shows levels of anti-Her-2/neu antibodies in serum in mice receiving a recombinant vaccinia virus expressing Her-2/neu, both Her-2/neu and IL-15, or a control vaccinia virus.
Figure 9:
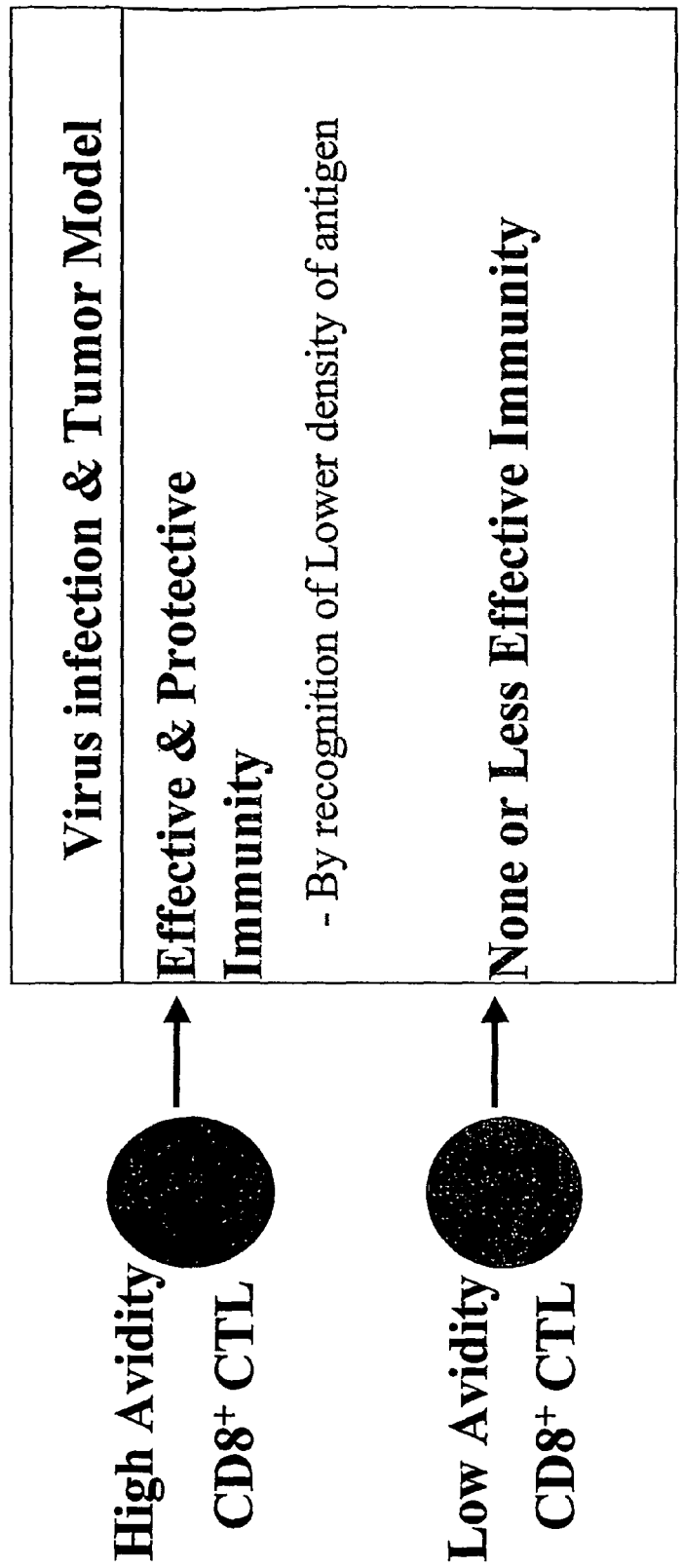
FIG. 9 illustrates that avidity of CD8$^+$ CTLs determines the effectiveness of CD8$^+$ CTL-mediated immunity.

Animals vaccinated with recombinant vaccinia expressing the Her-2/neu oncogene in tandem with IL-15 also demonstrated enhanced cellular and humoral responses in a mouse model of breast cancer. The specific over-expression of Her-2/neu oncogene in mammary tissues in this model leads to spontaneous tumor formation in mammary glands of the transgenic animals (see, e.g., Guy, et al., *Proc. Natl. Acad. Sci.* 89: 10578-10582, 1992). Animals vaccinated with a recombinant vaccinia virus expressing the Her-2/neu oncogene in tandem with IL-15 displayed a reduced tumor burden (see, FIGS. 6 and 7) and higher levels of Her-2/neu-specific antibodies (see, FIG. 8) in their sera than animals vaccinated with a recombinant vaccinia virus expressing Her-2/neu oncogene alone.

Thus it is clear that incorporating IL-15 in vaccine virus-based vaccine formulations, augments both cell-mediated immunity as well as antibody mediated humoral immunity against a vaccine antigen, whether it be a viral antigen or a cancer-specific antigen. In developing a vaccinia-based vaccine for either infectious diseases or cancer, if the desired response is to achieve a long lasting cell mediated and antibody mediated humoral response in the vaccines, for example as in the case of HIV or smallpox, then incorporating IL-15 results in a superior vaccine. It can also be beneficial in the case of subunit vaccines such as rabies vaccine where the required response is to achieve a solid antibody response, to incorporate IL-15. As has been shown in post-exposure rabies infections, administration of anti-rabies antibody can effectively prevent the development of rabies. See, e.g., *Recommendations of the Advisory Committee on Immunization Practices*, MMWR 1999 48(o RR-1): 1-21 (available at http://www.cdc.gov/mmwr). This illustrates that sufficiently effective antibody levels alone can provide protection against a vaccine antigen, such as rabies, without any involvement of cell-mediated immune responses.

Example 4

Enhancing Immune Responses in Non-Human Primates

The above examples reinforce the notion that incorporation of immunostimulatory cytokines in vaccine virus-based vectors can significantly enhance the immune responses in vaccines. To demonstrate the production of a long term protective immune response against a vaccine antigen in non-human primates, an MVA (modified-virus Ankara) recombinant 89.6 env-gag-pol virus which carries the HIV-1 envelope gene with SIV gag and pol genes (see, Amara, et al., *Science* 292: 6974, 2001) was used to generate dual recombinants expressing IL-15 by homologous recombination and insertion into the hemagglutinin locus with a pVOTE-modified vector comprising IL-15 sequences. Construction of multivalent MVA vectors is generally described in Amara, et al., *Science,* 2001, supra. For comparison purposes, dual recombinant strains expressing the same antigen(s) together with IL-2 (using a pVOTE modified vector to integrate at the hemagluttin locus) were also generated.

A cohort of 23 juvenile rhesus monkeys (*Macaca mulatta*) is used for immunization studies with the dual recombinant MVA viruses generated as described above. Animals that express the major histocompatibility complex (MHC) class I allele Mamu-A*01 are used, or, alternatively, animals are typed to identify those which express this allele using polymerase-chain reaction (PCR) analyses. Primers A*–01/R (5'-GAC AGC GAC GCC GCG AGC CAA-3') (SEQ ID NO: 2) and A*01/R (5'-GCT GCA GCG TCT CCT TCC CC-3') (SEQ ID NO: 3) are used to identify monkeys with Mamu-A*01

It is currently accepted that the tetramer technology is a reliable technique in quantitatively assessing CD8+ cells specific for a particular antigen. In rhesus monkeys, the most reliable and best-studied CTL epitopes for SIV mac gag polypeptide is restricted by the HLA-A homologue molecule Mamu-A*01. Thus, having monkeys with Mamu-A*01 haplotype permits use of tetrameric Mamu-A*01/SIV gag epitopes to precisely quantify the CD8+ T cell response in vaccinated animals. See, e.g., Juroda, et al., *J. Exp. Med.* 187: 1373-1381, 1998.

Animals are divided into 5 groups to be vaccinated intradermally with $10^9$ pfu of recombinant MVA vaccinia virus according to the following protocol:
  i) 5 animals receive MVA vaccinia expressing the SHIV antigens;
  ii) 5 animals receive dual recombinant MVA vaccinia expressing SHIV antigens with IL-2;
  iii) 5 animals receive dual recombinant MVA vaccinia expressing SHIV antigens with IL-15;
  iv) 4 animals remain as unvaccinated controls but will be infected with the pathogenic SHIV89.6P virus when vaccinated animals are challenged with this virus; and v) 4 animals remain unvaccinated and uninfected throughout the study and serve as healthy controls.

Following initial vaccination, animals are boosted twice in 4-week intervals with the respective viruses and their immunological parameters are monitored for 8 months after the final booster inoculation. Blood is collected from each individual animal every 4 weeks and the following assays are done to monitor cellular and humoral immune responses: Once the animals are challenged, monthly assessments of immunological parameters are continue in the infected animals until the termination of the study or euthanization of the diseased animal.

Sera is tested for antibodies to oligomeric HIV envelope gp140 using an ELISA assay initially as a screening test. See, as described in Chen, et al., *Nature Medicine* 7: 1225-1231, 2001. Virus neutralization assays on selected serum specimens from sequentially collected serum samples from each animal are performed, to determine the titer of neutralizing antibodies using MT-2 cells infected with SHIV 89.6 virus using the assay as described in Rose, et al., *Cell* 106: 539-549, 2001. Antibody titers are measured to ascertain the effect of IL-2 and IL-15 on the magnitude and the duration of the humoral response. However, neutralizing antibodies to SHIV89.6 virus will not likely influence the containment of challenge virus SHIV89.6P since these antibodies are non-cross-neutralizing.

For animals expressing the Mamu-A*01 histocompatibility type, the frequency of $CD8^+$ T cells recognizing the dominant Gag-CM9 epitope is determined by means of Mamu-A*01 tetramers. For animals other than of Mamu-A*01 type, frequency of T cells recognizing epitopes throughout the Gag polypeptide using pools of overlapping peptides. See, e.g., as described in Amara, et al., 2001, supra. Peripheral blood mononuclear cells (PBMC) are pulsed with pools of overlapping gag peptides followed by dual labeling for intracellular γ-interferon expression and expression of surface CD4 or CD8. Suitable monoclonal antibodies are commercially available, e.g., from Biosource International, Camarillo, Calif. Assay methodology is described in Rose, et al., *Cell* 106: 539-549, 2001.

To establish correlations between immune parameters ad disease progression in the vaccinated animals, animals treated as above are challenged with a pathogenic derivative of SHIV89.6, i.e., SHIV89.6P. SHIV89.6P carries an R5/X4 envelope and induces a rapid decline of $CD4^+$ T cells. In unvaccinated animals, this is associated with rapid onset of an AIDS-like disease. Animals are challenged 8 months post-vaccination, when vaccine-induced effector immune responses are not at peak levels, but when the memory phase is more important in dictating immune responses to a virus challenge. Thirty mucosal infectious doses of cell-free SHIV89.6P virus are administered intrarectally since most HIV-1 infections are transmitted across mucosal surfaces.

In addition to the assays described above, the following assays are performed.

Clinical Assessment Of Infected Animals

Monkeys are monitored clinically by routine hematological testing and blood chemistry analysis regularly (once a month) following virus challenge.

Post-Challenge Viral Load Quantitation

Viral loads in plasma are assessed weekly by detecting SHIV RNA using a real time PCR with a detection limit of 200 virus RNA copy equivalents per ml. If plasma viremia turns out to be negative, growth of virus from the PBMC of infected animals will be attempted by a co-culture technique.

$CD4^+$ T Lymphocyte Counts

Peripheral blood CD4 cell counts are done weekly following virus challenge to detect and monitor any depletion of CD4 cells in the infected animals. Rose, et al., *Cell* 106: 539-549, 2001.

By monitoring immunological parameters separately in each individual animal sequentially, reliable and meaningful information is maximized despite the small sample size and any genetic heterogeneity in the study cohort.

Lymph Node Biopsies

Lymph node biopsies are taken from infected animals at 3-month intervals and cytomorphological analyses are performed on them to evaluate the integrity of follicular architecture, expansion or atrophy of germinal centers, and to identify the presence and/or amount of follicular and paracortical depletions or hyperplasia. In addition, the presence of SHIV89.6P viral RNA is assessed by in situ hybridization in the lymph node material.

SHIV89.6P Virus Neutralizing Antibodies

ELISA antibody titers for oligomeric HIV envelope gp140 and the presence of neutralizing antibodies against SHIV 89.6 and SHIV89.6P are determined on a monthly basis, following challenge with the SHIV89.6P. See, e.g., Chen, et al., *Nat Med.* 7: 1225-31, 2001; Shibata, et al., *Nat. Med.* 5: 204-10, 1995.

Example 5

Enhancement of CTL Avidity by IL-15

An ideal vaccine against viral pathogens and cancers must induce high avidity $CD8^+$ cytotoxic T lymophocytes (CTLs) and the immunity provided by the vaccine should be long lasting. As illustrated in FIG. 9, high avidity $CD8^+$ CTLs provides more effective and protective immunity by recognition of lower densities of antigen in virus infection and tumor models. In contrast, low avidity CD8+CTLs provide less effective or no immunity. See, e.g., Ansari, et al., *Cell. Immunol.* 210(2): 125-42, 2001; Gray, et al., *J. Virol.* 75(21:10065-

72, 2001; Oh, et al. *J. Immunol.* 170(5): 2523-30, 2003; Pittet, et al., *J. Immunol.* 171(4):1844-9 (2003); Romieu, et al., *J. Immunol.* 161(10): 5133-7, 1998.

High avidity CD8+ CTLs can be selectively induced by increasing costimulatory signals and by boosting appropriately. As disclosed herein, long-lasting immunity can also be achieved by using IL-15 as a molecular vaccine adjuvant.

Figure 10:
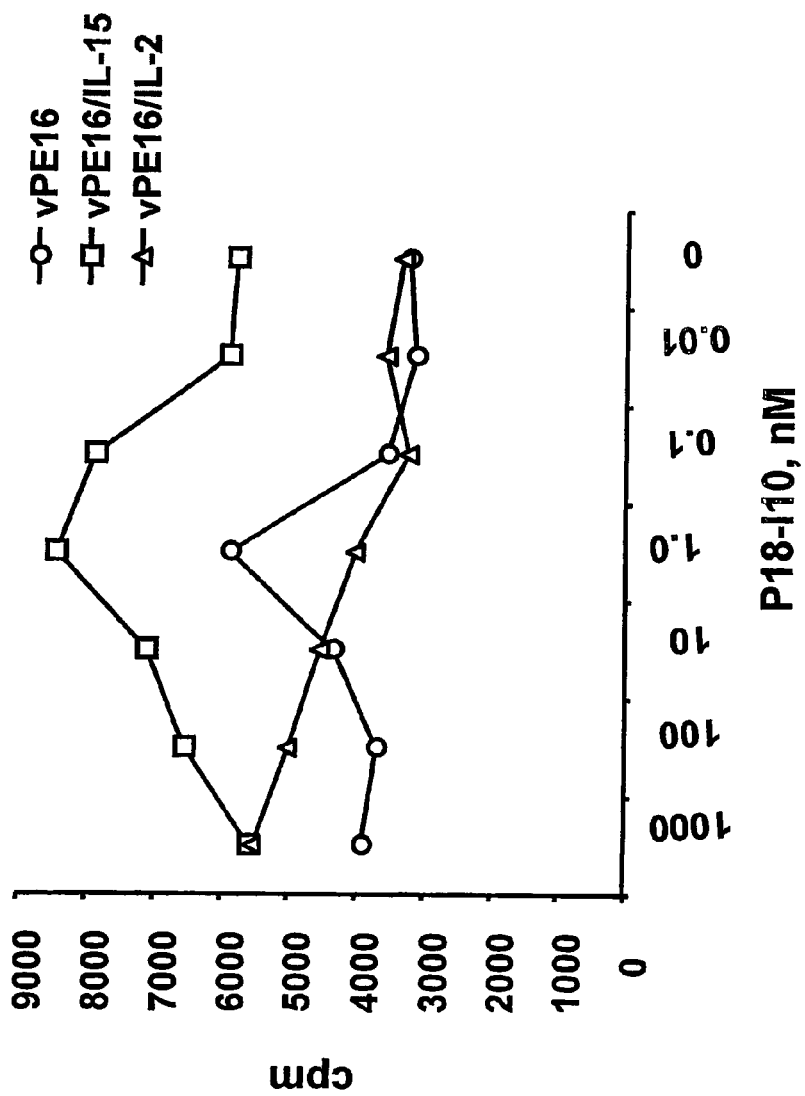
FIG. 10 is a graph showing that CD8$^+$ CTLs induced with IL-15 respond to lower density of antigen at 14 months after boosting.
Figure 14A:
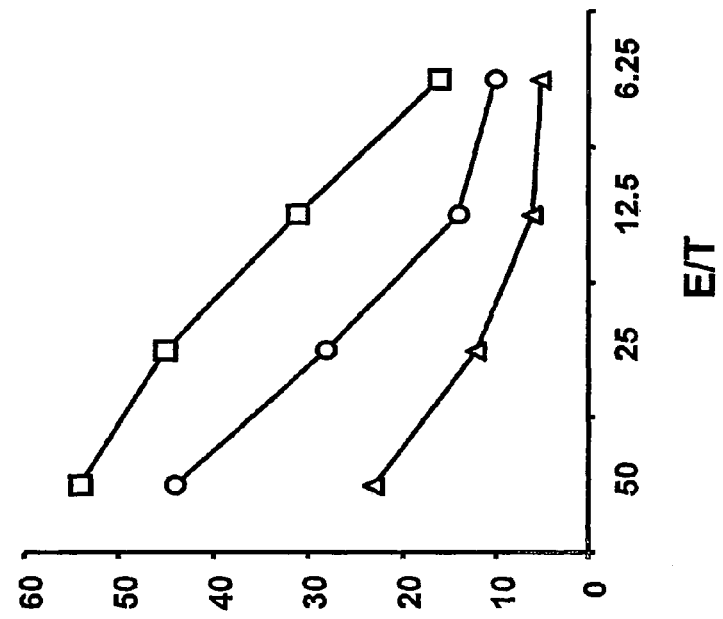
FIGS. 14A-B are graphs showing cytolytic activity of CD8$^+$ CTLs expanded with low concentration of peptide (0.001 μM).
Figure 14B:
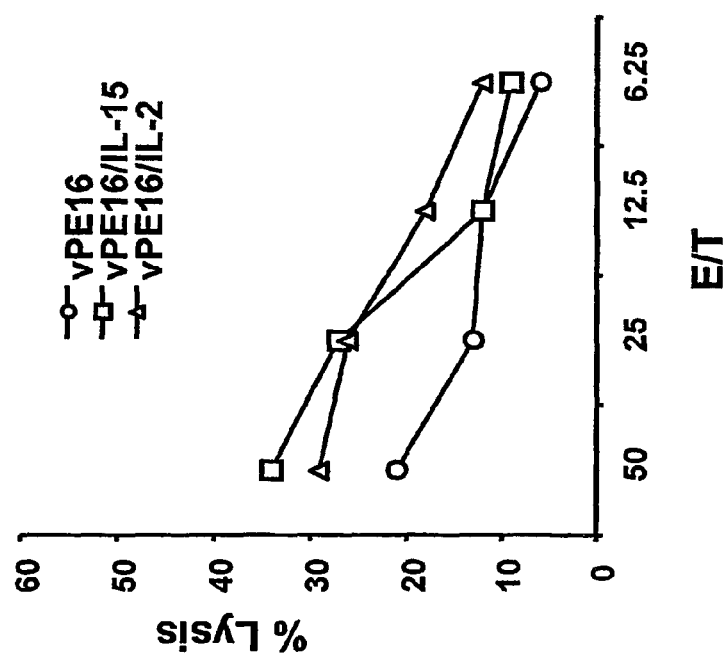

As demonstrated in the Examples above, IL-15 can be used as an adjuvant for an HIV vaccine because IL-15 results in long-lasting immunity. IL-15 is also associated with increased expression of anti-apoptotic proteins that can block high avidity CD8+ CTL death. Animals immunized with recombinant vaccinia expressing gp160 (vPE16), gp160 with IL-15 (vPE16/Il-15), or gp160 with IL-2 (vPE16/IL-2) induced a broad range of functional avidity in CD8+ CTsL. The range of avidity of CD8+ CTLs narrowed depending on the period after immunization. Surprisingly, however, CD8+ CTL induced with IL-15 responded to 10-fold lower and 100-fold lower amounts of antigen than CD8+ CTLs induced with vPE16 and vPE16/IL-2 did. As shown in FIG. 10, CD8+ CTLs induced with IL-15 respond to lower density of antigen at 14 months after boosting. As shown in FIGS. 11A-D, this difference increased with time after immunization. As shown in FIGS. 12A-C and FIGS. 13A-C, increased avidity over time correlates with increased specific cytolytic activity of CD8+ CTLs. This effect was more pronounced for CD8+ CTLs expanded with low concentrations of peptide (0.001 µM) (FIGS. 13A-C). Similarly, high avidity CD8+ CTLs induced with IL-15 persisted for longer periods of time in vivo, up to 14 months after boosting (FIGS. 14A and B).

Further, IL-15Rα expression levels on CD8+ T cells bearing different avidities were found to be different (not shown). High avidity CD8+ T cells expressed higher levels of IL-15α, but not IL-2Rβ or IL-7Rα, suggesting that IL-5Rα on CD8+ CTLs and IL-15 in vivo control the life of CD8+ CTLs with different avidities. Consistent with this result, data showed that high avidity CD8+ CTLs expressed increased levels of apoptotic proteins and proliferated better than low avidity CD8+ CTLs in response to IL-15. These findings support a mechanism in which IL-15 preferentially contributes to the maintenance of high avidity CD8+ CTLs. In addition, high avidity CD8+ CTLs express higher levels of CD8β.

These results indicate that IL-15, at the time of priming, selects or induces a different phenotype CTLs with greater avidity and longevity, providing more effective CTL immunity when IL-15 is included as an adjuvant.

Variations, modifications, and other implementations of what is described herein will occur to those of ordinary skill in the art without departing from the spirit and scope of the invention.

All of the references, patents, and patent applications identified above, are expressly incorporated herein by reference in their entireties.

What is claimed is:

1. A recombinant attenuated or nonvirulent vaccine virus vector comprising a nucleic acid sequence encoding mammalian IL-15 and an expression unit comprising a plurality of antigen encoding sequences operably linked to a first expression control sequence, wherein the expression unit comprises at least one CTL-recognized epitope, at least one T helper cell-recognized epitope, and at least one B cell-recognized epitope, wherein the vaccine virus is a poxvirus, wherein the first expression control sequence comprises viral regulatory elements, wherein the plurality of antigen coding sequences encode at least two antigens from two different polypeptides, wherein the IL-15 encoding sequence is operably linked to a second expression control sequence, and wherein the plurality of antigen coding sequences encode at least one antigen selected from the group consisting of an HIV, SIV, rabies, vaccinia, influenza, avian influenza, papillomavirus, cancer specific antigen, bacteria, *M. tuberculosis*, anthrax, and a malaria peptide or polypeptide, wherein expression of IL-15 induces persistent enhanced avidity CD8+ CTLs.

2. The recombinant attenuated or nonvirulent vaccine virus of claim 1, wherein the at least one antigen is an HIV or SIV peptide or polypeptide.

3. The recombinant attenuated or nonvirulent vaccine virus vector of claim 1, wherein the at least one antigen is a rabies peptide or polypeptide.

4. The recombinant attenuated or nonvirulent vaccine virus vector of claim 1, wherein the at least one antigen is a vaccinia peptide or polypeptide and elicits a protective immune response against smallpox.

5. The recombinant attenuated or nonvirulent vaccine virus vector of claim 1, wherein the at least one antigen is a cancer specific antigen peptide or polypeptide.

6. The recombinant attenuated or nonvirulent vaccine virus vector of claim 5, wherein the cancer specific antigen peptide or polypeptide is a Her-2/neu or prostate specific antigen polypeptide.

7. The recombinant attenuated or nonvirulent vaccine virus vector of claim 1, wherein the at least one antigen is a bacterial antigen.

8. The recombinant attenuated or nonvirulent vaccine virus vector of claim 1, wherein the at least two antigens are from two different clades of HIV.

9. The recombinant attenuated or nonvirulent vaccine virus vector of claim 1, wherein the CTL-recognized epitope, T helper cell-recognized epitope, and the B cell-recognized epitope are from the same HIV polypeptide.

10. The recombinant attenuated or nonvirulent vaccine virus vector of claim 1, wherein the vaccine virus vector comprises one or more capsid polypeptides.

11. The recombinant attenuated or nonvirulent vaccine virus vector of claim 1, wherein the antigen encoding sequence is expressed before the IL-15 encoding sequence.

12. The recombinant attenuated or nonvirulent vaccine virus vector of claim 1, wherein the antigen encoding sequence is expressed after the IL-15 encoding sequence.

13. A vaccine composition comprising the recombinant attenuated or nonvirulent vaccine virus vector of claim 1, and a nucleic acid encoding at least one antigen.

14. The composition according to claim 13, further comprising a pharmaceutical carrier.

15. The composition of claim 1, wherein the at least one antigen is an avian flu, human papillomavirus, *M. tuberculosis*, anthrax, or malaria peptide or polypeptide.

16. A recombinant attenuated or nonvirulent vaccine virus vector comprising a nucleic acid sequence encoding mammalian IL-15 and an expression unit comprising a plurality of antigen encoding sequences operably linked to a first expression control sequence, wherein the expression unit comprises at least one CTL-recognized epitope, at least one T helper cell-recognized epitope, and at least one B cell-recognized epitope, wherein the vaccine virus is a poxvirus, wherein the first expression control sequence comprises viral regulatory elements, wherein the IL-15 encoding sequence is operably linked to a second expression control sequence, wherein the plurality of antigen encoding sequences encode at least two antigens from two different polypeptides, and wherein the plurality of antigen encoding sequences encode at least one antigen selected from the group consisting of: an influenza, *M. tuberculosis*, and anthrax peptide or polypeptide, wherein expression of IL-15 induces persistent enhanced avidity CD8+ CTLs.

* * * * *

```
SEQUENCE LISTING

<160> NUMBER OF SEQ ID NOS: 3

<210> SEQ ID NO 1
<211> LENGTH: 108
<212> TYPE: DNA
<213> ORGANISM: Artificial Sequence
<220> FEATURE:
<223> OTHER INFORMATION: Description of Artificial Sequence: Synthetic
      ologonucleotide

<400> SEQUENCE: 1
cacccataaa taataaatac aataattaat ttctcgtaaa agtagaaaat atattctaat       60
ttattgcacg gtaaggaagt agaatcataa agaacagtga cggatccc                  108

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacagcgacg ccgcgagcca a                                                21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctgcagcgt ctccttcccc                                                  20
```